United States Patent
Fei et al.

(10) Patent No.: US 11,873,307 B2
(45) Date of Patent: Jan. 16, 2024

(54) MANUFACTURE OF COMPOUNDS AND COMPOSITIONS FOR INHIBITING THE ACTIVITY OF SHP2

(71) Applicant: Novartis AG, Basel (CH)

(72) Inventors: Zhongbo Fei, Shanghai (CN); Huanqing Jia, Changshu (CN); Wei Li, Changshu (CN); Xiaohui Lin, Changshu (CN); Zhongcheng Min, Changshu (CN); Hui Wang, Changshu (CN); Jianhua Wang, Changshu (CN); Hao Zhang, Changshu (CN)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/280,632

(22) PCT Filed: Sep. 18, 2019

(86) PCT No.: PCT/IB2019/057863
§ 371 (c)(1),
(2) Date: Mar. 26, 2021

(87) PCT Pub. No.: WO2020/065452
PCT Pub. Date: Apr. 2, 2020

(65) Prior Publication Data
US 2021/0355134 A1   Nov. 18, 2021

(30) Foreign Application Priority Data
Sep. 29, 2018   (WO) ................ PCT/CN2018/108738

(51) Int. Cl.
C07D 491/107   (2006.01)
(52) U.S. Cl.
CPC ................ C07D 491/107 (2013.01)
(58) Field of Classification Search
None
See application file for complete search history.

(56) References Cited

FOREIGN PATENT DOCUMENTS

| | | |
|---|---|---|
| CN | 105916845 A | 8/2016 |
| CN | 110713447 A | 1/2020 |
| WO | WO 2015/107493 A1 | 7/2015 |
| WO | WO 2015/107494 A1 | 7/2015 |
| WO | WO 2015/107495 A1 | 7/2015 |
| WO | WO 2016/203404 A1 | 12/2016 |
| WO | WO 2016/203405 A1 | 12/2016 |
| WO | WO 2016/203406 A1 | 12/2016 |
| WO | WO 2017/211303 A1 | 12/2017 |
| WO | WO 2017/216706 A1 | 12/2017 |
| WO | WO 2018/013597 A1 | 1/2018 |
| WO | WO 2018/130928 A1 | 7/2018 |
| WO | WO 2018/136265 A1 | 7/2018 |
| WO | WO 2018/172984 A1 | 9/2018 |
| WO | WO 2019/075265 A1 | 4/2019 |
| WO | WO 2020/065452 A1 | 4/2020 |
| WO | WO 2020/065453 A1 | 4/2020 |
| WO | WO 2020/165732 A1 | 8/2020 |
| WO | WO 2020/165733 A1 | 8/2020 |
| WO | WO 2020/165734 A1 | 8/2020 |
| WO | WO 2020/177653 A1 | 9/2020 |
| WO | WO 2021/171261 A1 | 9/2021 |
| WO | WO 2021/224867 A1 | 11/2021 |
| WO | WO 2022/009098 A1 | 1/2022 |

OTHER PUBLICATIONS

International Search Report and Written Opinion for International Application No. PCT/IB2019/057863, dated Feb. 6, 2020, 19 pages.
Palamidessi et al., "Pyrazine derivatives. X. Trichloropyrazine", Farmaco, Edizione Scientifica, 21(11):805-810, 1966, XP009518495.
European Office Action for EP Application No. 19773559.0, dated May 10, 2023, 5 pages.
International Search Report and Written Opinion for International Application No. PCT/CN2020/100882, dated Apr. 9, 2021, 10 pages.
International Search Report and Written Opinion for International Application No. PCT/CN2021/094139, dated Aug. 20, 2021, 9 pages.

(Continued)

Primary Examiner — Samantha L Shterengarts
(74) Attorney, Agent, or Firm — LATHROP GPM LLP; Brian C. Trinque

(57) ABSTRACT

The present invention relates to a method for the manufacture of a compound of Formula I or a pharmaceutically acceptable salt, acid co-crystal, hydrate or other solvate thereof, said method comprising reacting a compound of the formula II with a compound of the formula III according to the following reaction scheme: wherein LG, A, n, m and p are as defined in the Summary of the Invention.

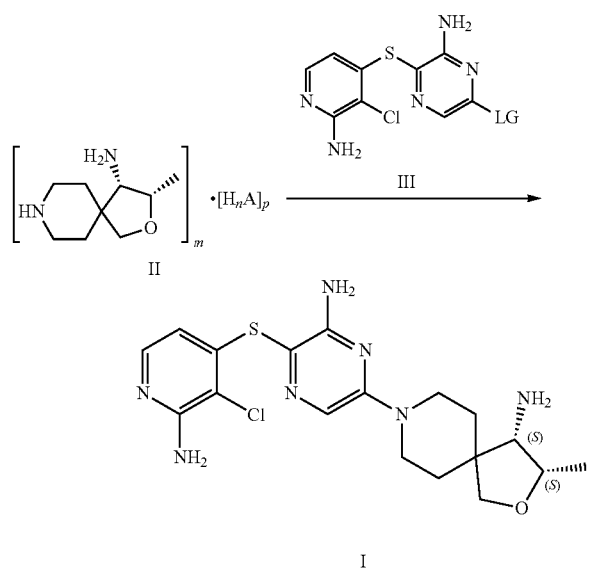

23 Claims, No Drawings

(56) References Cited

OTHER PUBLICATIONS

International Search Report and Written Opinion for International Application No. PCT/IB2021/056057, dated Aug. 10, 2021, 10 pages.
Lamarche et al., "Identification of TNO155. An Allosteric SHP2 Inhibitor for the Treatment of Cancer", *Journal of Medicinal Chemistry* 63(22):13578-13594 (2020).

MANUFACTURE OF COMPOUNDS AND COMPOSITIONS FOR INHIBITING THE ACTIVITY OF SHP2

BACKGROUND

Field of the Invention

The present invention relates to a process for the manufacture of a compound capable of inhibiting the activity of SHP2 and intermediates useful therein.

Background of the Invention

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

The compound with the name (3S,4S)-8-(6-amino-5-((2-amino-3-chloropyridin-4-yl)thio)pyrazin-2-yl)-3-methyl-2-oxa-8-azaspiro[4.5]decan-4-amine, which has the formula I:

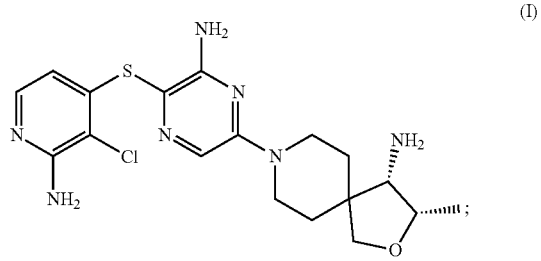 [SMILES: C[C@@H]1OCC2(CCN(c3cnc(Sc4ccnc(N)c4Cl)c(N)n3)CC2)[C@@H]1N]

as well as pharmaceutically acceptable salts thereof are described in WO2015/107495 A1 as an inhibitor of SHP2. Various therapeutic and treatment methods are also described.

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compound that can be manufactured according to the present invention fulfills the need of small molecules to that inhibit the activity of SHP2.

WO2015/107495 A1 describes a method for the manufacture of the compound of the formula I which can be characterized by the following reaction scheme:

Scheme 1

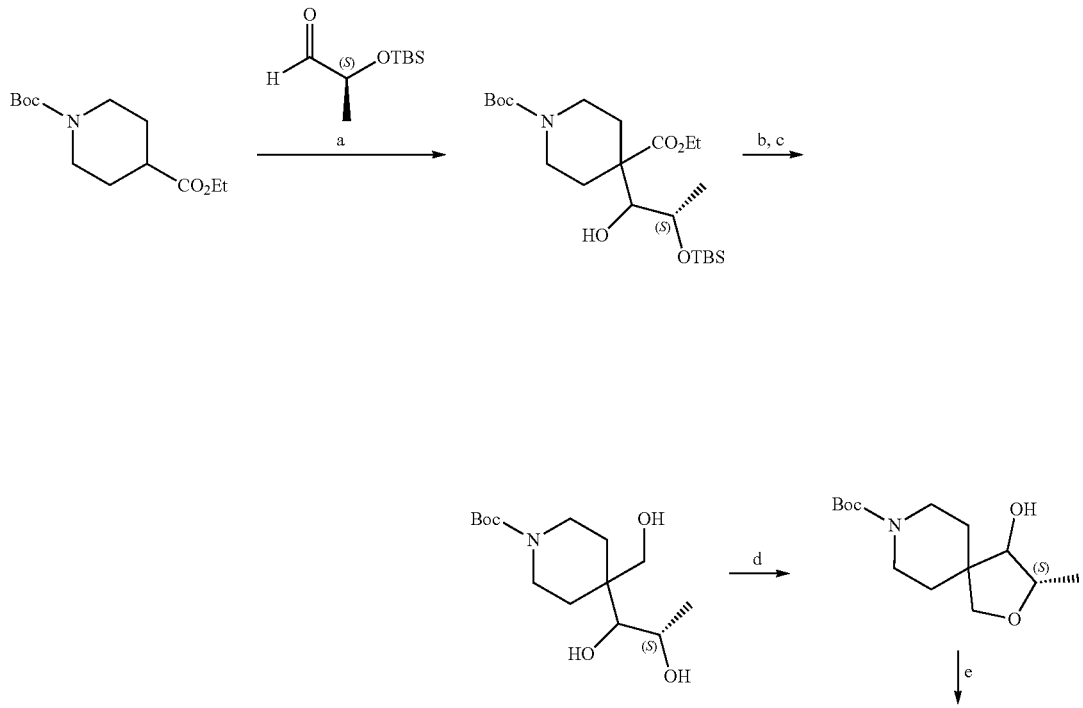

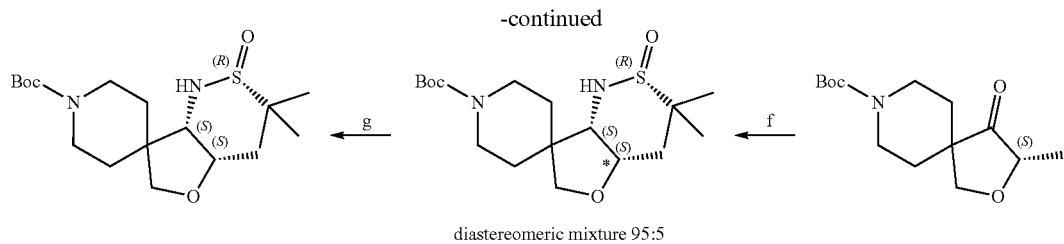

The last compound resulting from step g above was then reacted as follows:

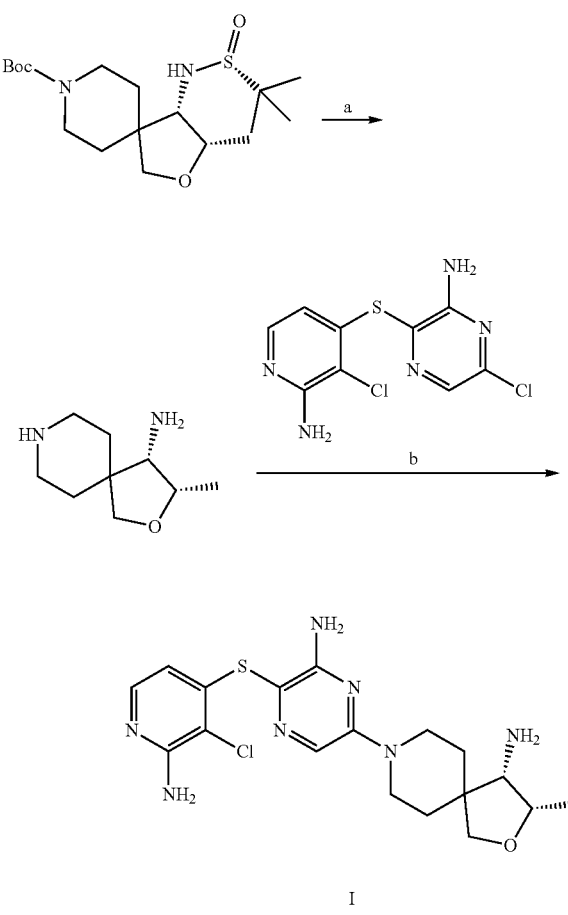

Thus the compound of formula I is obtained (last compound in the scheme above). The synthesis requires at least the 9 steps shown and is appropriate for laboratory scale synthesis.

The manufacture is difficult and, for example, requires the separation of the diastereomers at step g in the reaction scheme above. Furthermore, many of the intermediates do not crystallize so that they have to be used without the advantage of higher purity from crystallization.

In addition, chromatographic steps are used in the process.

Furthermore, the aldehyde starting material for reaction a in Scheme 1 above is a compound known from the literature but not available in bulk (normally up to gram scale, for example, from Aldlab Chemicals), showing some inherent instability so that advantageously it is prepared and used right away. Large scale synthesis requires, for example, kilogram or more amounts.

In addition, the cyclisation (step d in Scheme 1) has only moderate yield, with educt, the tosylate of the desired product and further impurities also being present, so that separation is required.

The ketone substrate product of step e in Scheme 1) is partially racemized, even if enantiomeric pure aldehyde starting material is used, resulting in the formation of 4 diastereomers in step f (which actually comprises two steps, reduction and condensation), leading to a 95:5 ratio of the two major diastereomers which would require further separation.

Furthermore, the synthesis involves many oily intermediates thus not ideal for purification as indicated in the following scheme:

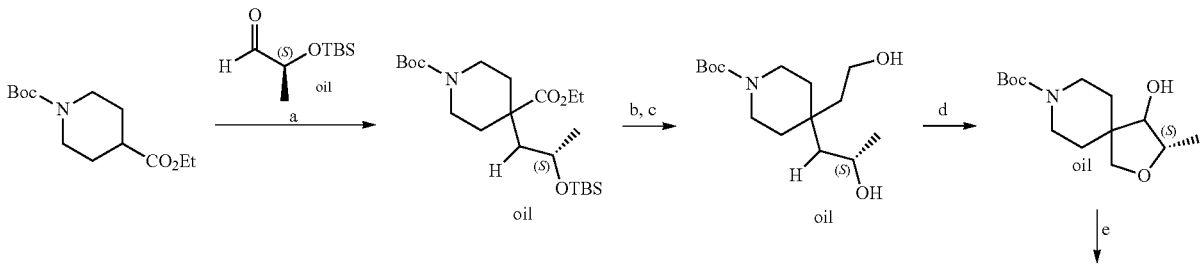

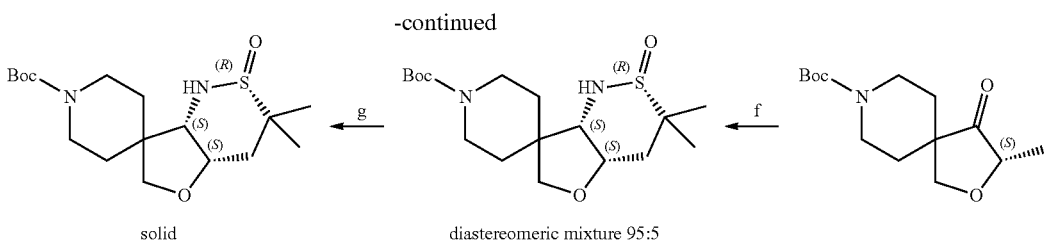

Therefore, the process, though feasible especially on a laboratory scale, is not ideal for manufacture at a large scale.

The compound added in reaction b in Scheme 2 is obtained according to WO2015/1107495 A1 as "Intermediate 10" as follows:

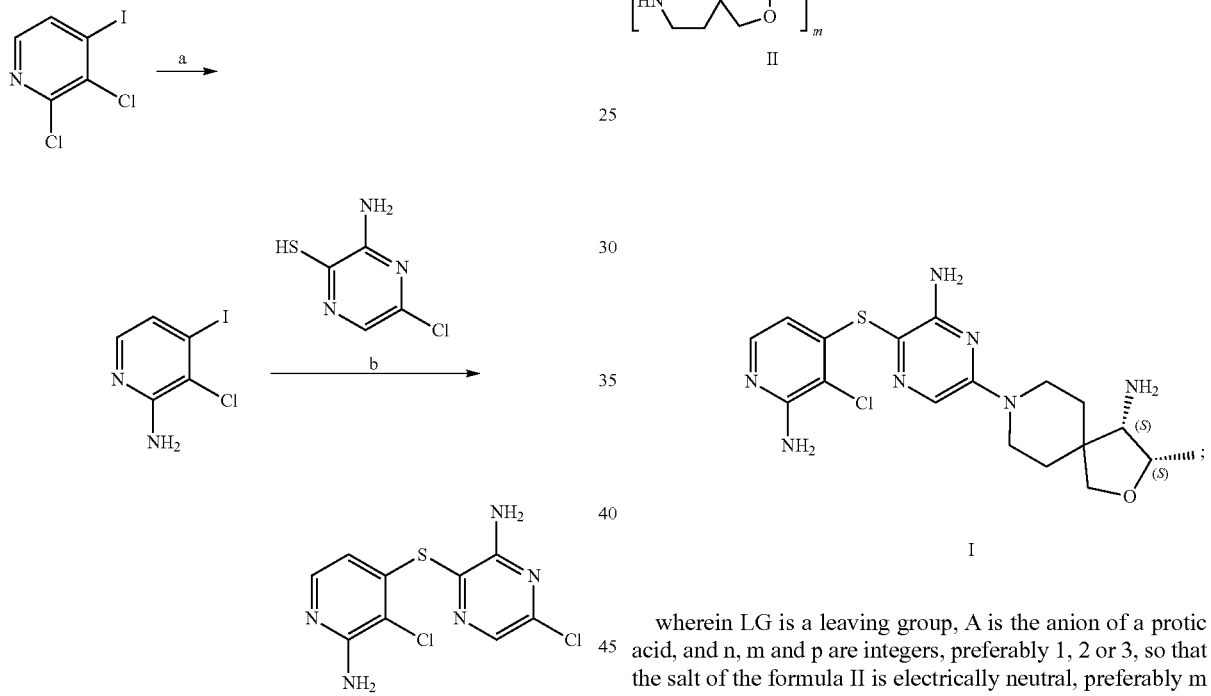

While this synthesis is also feasible, certain amendments would be desirable as the amination step 'a' results in only moderate yields (for example around 30 to 40%).

SUMMARY OF THE INVENTION

In one aspect, the present invention provides a method for the manufacture of a compound of Formula I as mentioned above, or a pharmaceutically acceptable salt, acid co-crystal, hydrate or other solvate thereof.

In a further aspect, the present invention provides a method for the manufacture of a compound of Formula I as mentioned above, or a pharmaceutically acceptable salt, acid co-crystal, hydrate or other solvate thereof, said method comprising reacting a compound of the formula II with a compound of the formula III according to the following reaction scheme:

wherein LG is a leaving group, A is the anion of a protic acid, and n, m and p are integers, preferably 1, 2 or 3, so that the salt of the formula II is electrically neutral, preferably m is 1, n is 1 and p is 2; where the compound of the formula II is preferably obtained either (i) by deprotecting or (ii) by reducing a compound of the formula IV:

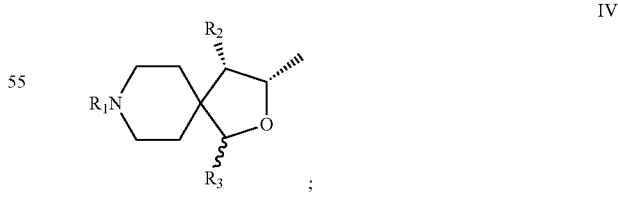

wherein in case (i) $R_1$ is a secondary amino protecting group and $R_2$ is a protected amino group and $R_3$ is hydrogen, or in case (ii) $R_1$ is a secondary amino protecting group, $R_2$ is amino and $R_3$ is hydroxyl, and if required (that is, if the acid is not already present for example due to the deprotection) reacting the resulting compound of the formula III:

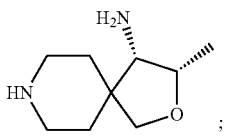

with an acid of the formula $H_nA$ to yield the compound of the formula II.

In both cases (i) and (ii) just mentioned and as a preferred second aspect of the invention, the manufacturing of a compound of the formula II, in a first step preferably followed by the further steps defined by further invention embodiments defined below, comprises reacting a compound of the formula V:

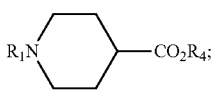

wherein $R_1$ is a secondary amino protecting group and $R_4$ is a carboxyl (—COOH) protecting group, in the presence of a strong base with L lactide of the formula:

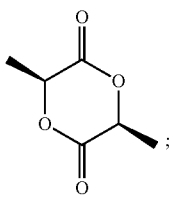

to yield a compound of the formula VI:

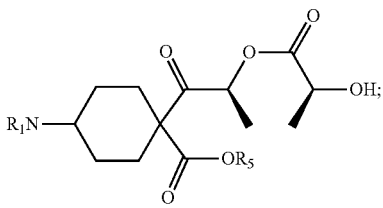

wherein $R_1$ is as defined for a compound of the formula IV and $R_5$ is unsubstituted or substituted alkyl, unsubstituted or substituted cycloalkyl or unsubstituted or substituted aryl, or alternatively yielding a compound of the formula VI*:

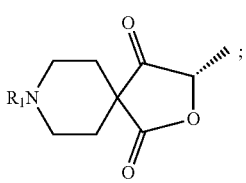

wherein $R_1$ is as defined for a compound of the formula IV.

Each of these two reaction variants as such is also an embodiment of the invention.

As a further embodiment of the invention or preferably in a further step, a compound of the formula VI as just described is cyclized with hydroxylamine, or a salt thereof, or alternatively a compound of the formula VI* is cyclized with hydroxylamine, or a salt thereof, to yield a hydroxylamine compound of the formula VII, respectively:

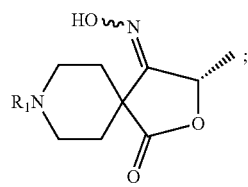

wherein $R_1$ is as defined for a compound of the formula IV.

As a further embodiment of the invention or preferable in a further step, a compound of the formula VII is either (a-i) hydrogenated to yield an amino compound of the formula VIII:

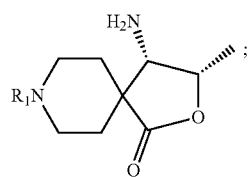

wherein $R_1$ is as defined for a compound of the formula IV, or (a-ii) acylated under reducing conditions to yield a compound of the formula VIII*:

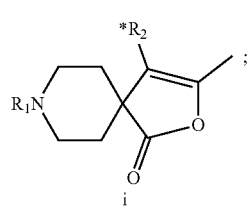

wherein $R_1$ is as defined for a compound of the formula IV and $*R_2$ is acylated amino (=acyl protected amino).

In another preferred embodiment of the invention or preferably in a further step after reaction (a-i) just described, a compound of the formula VIII is either (b-i) reduced to yield a compound of the formula IX:

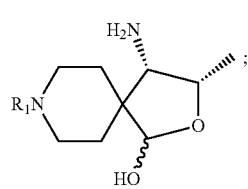

wherein R₁ is as defined for a compound of the formula IV, which compound is a compound of the formula IV wherein R₁ is a secondary amino protecting group, R₂ is amino and R₃ is hydroxyl; where the reducing step (ii) mentioned for a compound of the corresponding formula IV above falling under the definition of the compound of formula IX is preferably, as an own invention embodiment or more preferably in a further step, conducted using a trialkylsilane to yield, after subsequent addition of an acid of the formula HA as defined above a compound of the formula II as described above;

or (c-i), as an own invention embodiment or preferably in a further step, reacted with an amino protecting group inserting compound to yield a compound of the formula X:

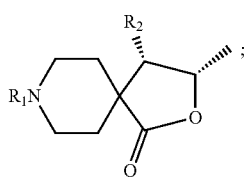

X wherein R₁ is as defined for a compound of the formula IV and R₂ is a protected amino group, which compound of formula X is, as an own invention embodiment or preferably in a further step, reduced to a compound of the formula XI:

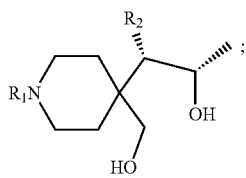

XI wherein R₁ is as defined for a compound of the formula IV and R₂ is a protected amino group; which compound of formula XI, as an own invention embodiment or preferably in a further step, is reacted at the hydroxy of the hydroxymethyl group (directly bound to the ring) with a leaving group forming agent of the formula LG*-X in which LG* is an electrophilic radical capable, with the hydroxy to which it is bound, of forming a leaving group LG2 and X is halogen, to yield a compound of the formula XII:

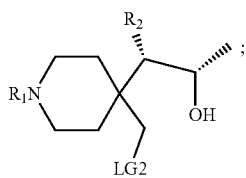

XII wherein R₁ is as defined for a compound of the formula IV, R₂ is a protected amino group and LG2 is a leaving group;

which compound of formula XII is then, as an own invention embodiment or preferably in a further step, cyclized under basic conditions to yield a compound of the formula XIII:

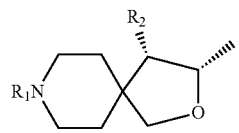

XIII wherein R₁ is a secondary amino protecting group and R₂ is a protected amino group, which is a compound of the formula IV wherein R₁ is a secondary amino protecting group and R₂ is a protected amino group and R₃ is hydrogen, where the deprotecting step (i) mentioned for a compound of the corresponding formula IV above of the compound of formula XIII is preferably, as an own invention embodiment or more preferably in a further step, conducted using an acid H$_n$A as defined for c compound of the formula II to yield a compound of the formula II as described above.

In another preferred embodiment of the invention or preferably in a further step after reaction (a-ii) described above, a compound of the formula VIII* is (b-ii), as an own invention embodiment or preferably in a further step, is hydrogenated in the presence of a chiral hydrogenation catalyst to yield a compound of the formula X*:

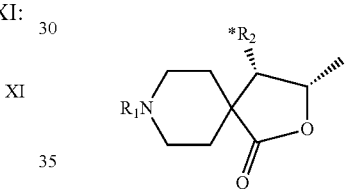

X* wherein R₁ is as defined for a compound of the formula IV and *R₂ is an acylated amino group, which compound of formula X* is, as an own invention embodiment or preferably in a further step, reduced to a compound of the formula XI*:

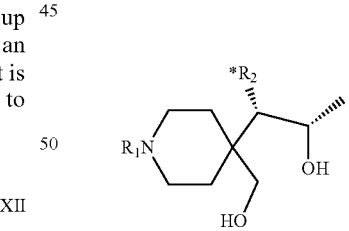

XI* wherein R₁ is as defined for a compound of the formula IV and *R₂ is an acylated amino group;

which compound of formula XI* is, as an own invention embodiment or preferably in a further step, reacted at the hydroxy of the hydroxymethyl group (the one directly bound to the ring in formula XI*) with a leaving group forming agent of the formula LG*-X in which LG* is an electrophilic radical capable of forming, with the hydroxy to which it is bound, a leaving group LG2 and X is halogen, to yield a compound of the formula XII*:

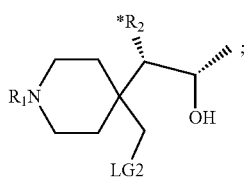

XII* wherein R₁ is as defined for a compound of the formula IV, R₂ is a protected amino group and LG2 is a leaving group;

which compound of formula XII* is then, as an own invention embodiment or preferably in a further step, cyclized under basic conditions to yield a compound of the formula XIII*:

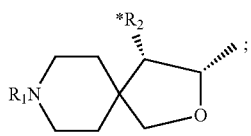

XIII* in which R₁ is a secondary amino protecting group and *R₂ is an acylated amino group, which corresponds to a compound of the formula IV wherein R₁ is a secondary amino protecting group and R₂ is an acylated (=acyl protected) amino group and R₃ is hydrogen; where the deprotecting step (i) mentioned for a compound of the corresponding formula IV above (where deprotecting here means deacylating) of the compound of formula XIII* is preferably, as an own invention embodiment or more preferably in a further step, conducted using an acid KA as defined for a compound of the formula II to yield a compound of the formula II as described above.

The following novel intermediates each also represent invention embodiments:

A (salt) compound of the formula II:

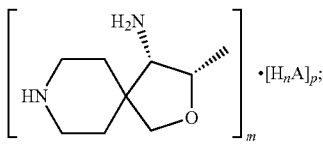

II wherein A is the anion of a protic acid, especially Cl, and n, m and p are integers, preferably 1, 2 or 3, so that the salt of the formula II is electrically neutral, especially wherein n and m are 1 and p is 2.

A compound of the formula VI:

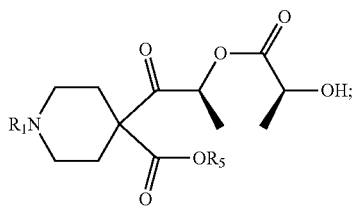

VI wherein R₁ is a secondary amino protecting group, especially tert-butyloxycarbonyl, and R₅ is unsubstituted or substituted alkyl, unsubstituted or substituted cycloalkyl or unsubstituted or substituted aryl, especially ethyl.

A compound of the formula VI*:

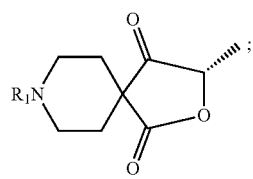

VI* wherein R₁ is a secondary amino protecting group, especially tert-butoxycarbonyl.

A compound of the formula VII:

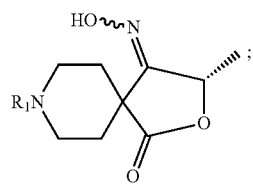

VII wherein R₁ is a secondary amino protecting group, especially tert-butoxycarbonyl.

A compound of the formula VIII:

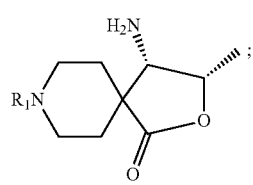

VIII wherein R₁ is a secondary amino protecting group, especially tert-butoxycarbonyl.

A compound of the formula IX:

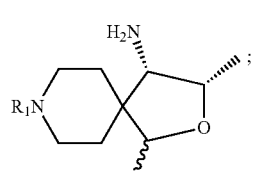

IX wherein R₁ is a secondary amino protecting group, especially tert-butoxycarbonyl.

A compound of the formula VIII*:

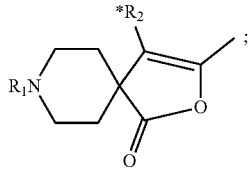

wherein $R_1$ is a secondary amino protecting group, especially tert-butoxycarbonyl, and *$R_2$ is acylated amino, especially acetylamino.

A compound of the formula X*:

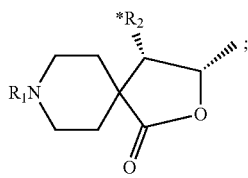

wherein $R_1$ is a secondary amino protecting group, especially tert-butoxycarbonyl, and *$R_2$ is acylated amino, especially acetylamino.

A compound of the formula XI*:

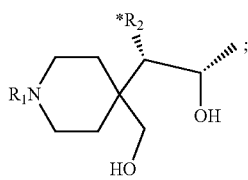

wherein $R_1$ is a secondary amino protecting group, especially tert-butoxycarbonyl, and *$R_2$ is acylated amino, especially acetylamino.

A compound of the formula XII*:

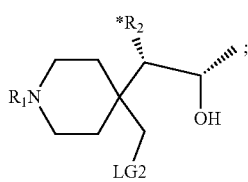

wherein $R_1$ is a secondary amino protecting group, especially tert-butoxycarbonyl, *$R_2$ is acylated amino, especially acetylamino, and LG2 is a leaving group, especially toluolsulfonyloxy.

A compound of the formula XIII*:

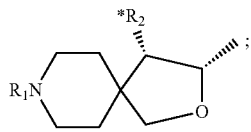

in which $R_1$ is a secondary amino protecting group, especially tert-butoxycarbonyl, and *$R_2$ is an acylated amino group, especially acetylamino.

A compound of the formula X:

[Structure X]

wherein $R_1$ is a secondary amino protecting group, especially tert-butoxycarbony, and $R_2$ is a protected amino group, especially tert-butoxacarbonylamino.

A compound of the formula XI:

[Structure XI]

wherein $R_1$ is a secondary amino protecting group, especially tert-butoxycarbonyl, and $R_2$ is a protected amino group, especially tert-butoxycarbonylamino.

A compound of the formula XII:

[Structure XII]

wherein $R_1$ is a secondary amino protecting group, especially tert-butoxycarbonyl, $R_2$ is a protected amino group, especially tert-butoxycarbonylamino, and LG2 is a leaving group, especially toluolsulfonyloxy.

A compound of the formula XIII:

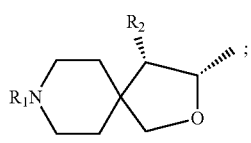

wherein $R_1$ is a secondary amino protecting group, especially tert-butoxycarbonyl, and $R_2$ is a protected amino group, especially tert-butoxycarbonylamino.

The mentioned compounds can be present in free form or as salts thereof where salt-forming groups (such as imini or amino) are present, especially the acid addition salts, such as salts with an inorganic acid, such as a hydrogenhalide, for example HCl, sulfuric acid or phosphoric acid, and/or with an organic acid, such as a sulfonic acid, such as methyl- or ethylsulfonic acid or toluenesulfonic acid, a phosphonic acid or a carboxylic acid, for example an alkanoic acid, such as acetic acid or citric acid, just to mention some examples.

DESCRIPTION OF PREFERRED EMBODIMENTS

The following definitions define more general features in a preferred more specific way, and it possible to replace one, more than one or all of the more general features in the invention variants=embodiments by a more specific definition, which defines more specific invention embodiments.

The conditions for the reactions described above are especially chosen as follows:

The reaction of a compound II with a compound of the formula III, wherein LG is a leaving group, preferably halo, especially chloro or bromo, preferably takes place in the presence of a weak base, such as an alkali metal carbonate or metal-hydrogencarbonate, in an aprotic solvent, such as an N,N-Dialkylamide of an alkanoic acid, for example dimethal acetamide or dimethyl formamide, at preferably elevated temperatures, for example in the range from 30° C. to the boiling point of the reaction mixtures, for example from 50 to 100° C.

The deprotecting (i) of a compound of the formula IV wherein $R_1$ is a secondary amino protecting group and $R_2$ is a protected amino group and $R_3$ is hydrogen to yield a compound of the formula II preferably takes place in the presence of a strong acid $H_nA$, such as trifluoroacetic acid, trifluoromethane sulfonic acid or preferably an inorganic acid, for example sulfuric acid, phosphoric acid or especially a hydrogen halide, most especially hydrogen chloride, in a solvent, for example an alcohol or a mixture of alcohols (especially if $R_2$ is a benzyloxycarbonyl or especially alkoxycarbonyl, such as tert-butoxycarbonyl) or in the presence of water (especially if $R_2$ is an acyl, especially lower alkanoyl, for example acetyl) at preferred temperatures in the range from 10° C. to the boiling temperature of the solvent, for example from 20° C. to (especially where $R_2$ is acyl) 115° C.

The alternative reducing (ii) of a compound of the formula IV wherein $R_1$ is a secondary amino protecting group, $R_2$ is amino and $R_3$ is hydroxyl preferably takes place with a trialkylsilane, especially triethylsilane, in the presence of a strong inorganic or preferably (strong) organic acid, especially trifluoromethane sulfonic acid, in an appropriate aprotic solvent, such as an ether or especially acetonitrile, and subsequent addition of the acid $H_nA$ to yield the (salt or cocrystal) compound of formula II.

The reaction of the compound of the formula V with L-Lactide to yield a compound of the formula VI or VI* preferably takes place in the presence of a strong base, especially an alkyl-alkaline metals, such as n-butylllithium, and a nitrogen base, especially di-isopropylamine or diethylamine, in a solvent, such as an acyclic or especially cyclic ether, preferably tetrahyrofurane, at preferably low temperatures, for example in the range from −80 to −5° C. If the reaction is conducted nearer to −80° C., the result is a compound of the formula VI, if the reaction is conducted under raising of the temperature up to nearer −5° C., the result is the compound of the formula VI*.

The cyclization of a compound of the formula VI with hydroxylamine, or a salt thereof, or the reaction of a compound of the formula VI* with hydroxylamine, or a salt thereof, to the compound of the formula VII, respectively, preferably takes place with an acid addition salt of hydroxylamine, for example a hydrogen halide salt thereof, such as the hydrochloride salt thereof, in the presence of a weak base, for example an alkali metal alkanoate, such as sodium acetate, in a polar organic solvent, for example an alcohol, such as an alkanol, for example methanol or ethanol, at preferred temperatures in the range from 0 to 80° C., for example from 10 to 50° C.

The hydrogenation (a-i) of the hydroxylamine compound of the formula VII to the corresponding amine of the formula VIII preferably takes place as heterogeneous hydrogenation in the presence of a hydrogenation catalyst, for example platinum, palladium, rhodium, or ruthenium or other highly active catalysts, which operate at lower temperatures (for example from 0 to 40° C.) and lower pressures (for example, 1 bar) of Hz, or non-precious metal catalysts, especially those based on nickel (such as Raney nickel and Urushibara nickel) at elevated temperatures and higher $H_2$ pressure, for example in the range from 5 to 50 bar, such as from 10 to 20 bar. The reaction is conducted in a polar solvent, especially an alcohol, for example an alkanol, such as ethanol or especially methanol.

The acylation (a-ii) of the hydroxyl compound of the formula VII under reducing conditions to the compound of the formula VIII* preferably takes place in the presence of an acylating agent, especially an anhydride of a carboxylic acid, such as an alkanoic acid anhydride, especially acetanhydride, in the presence of an ignoble metal, such as zinc (for example as zinc amalgam) or especially iron, and an acid, either an inorganic acid, such as a hydrogen halogenide, for example hydrogen chloride, sulfuric acid or an organic acid, such as the carboxylic acid corresponding to the anhydride, especially an alkanoic acid, especially acetic acid, as reductant, in an inert organic solvent, such as a hydrocarbon or an aromatic compound, for example toluene or xylylene, at preferably elevated temperatures in the range from 25° C. to the boiling point of the reaction mixture, for example in the range from 40 to 80° C.

Acyl, in the context of the present invention, refers to a moiety of an organic acid where in the acyl rest itself the carboxyl (—COOH) group is bound to a carbon (for example as in acetyl=$H_3$CCOO—), not (as for example in tert-butoxycarbonyl) to an oxygen.

The reduction (b-i) of a compound of the formula VIII to a compound of the formula IX preferably takes place with a complex hydride reducing the oxo in formula VIII to the hydroxy in formula IX, such as diisobutylaluminium hydride, in an aprotic solvent, such as an ether or especially a cyclic ether, such as tetrahydrofurane, at preferably low temperatures in the range from −100 to −20° C., for example from −80 to −70° C.

In the case where then the compound of the formula IX, as compound corresponding to the respective compound of the formula IV, is reduced to the compound of the formula II, the reduction preferably takes place with a trialkylsilane, especially triethylsilane, in an acid, especially a strong organic sulfonic acid, such as trifluoromethane sulfonic acid, in an aprotic solvent, such as a hydrocarbon, an ester or especially a nitrile, such as acetonitrile, at preferably elevated temperatures in the range from 30° C. to the boiling point of the reaction mixture, for example from 50 to 95° C. The subsequent reaction with the acid $H_nA$ preferably takes place in a protic, potentially aqueous solvent, such as isopropyl alcohol.

The reaction (c-i) of a compound of the formula VIII with an amino group inserting agent, especially an dialkanoyldicarbonate, especially di-tert-butyldicarbonate (=Boc anhydride) is preferably conducted in the presence of an tertiary amine, such as a tri-alkyl-amine, especially diisopropylethylamine, in an aprotic solvent, especially a halogenated hydrocarbon, such as dichloromethane, at preferred temperatures in the range from 0 to 50° C., for example from 20 to 30° C., resulting in a compound of the formula X.

The reducing of a compound of the formula X to a compound of the formula XI preferably takes place in the presence of a complex hydride capable of reducing the lactone group in formula X to the open ring in formula XI with two hydroxy groups, such as lithium borohydride, in an aprotic solvent, such as a linear or preferably a cyclic ether, for example tetrahydrofurane, preferably at a temperature in the range from 0 to 50° C., for example at 20 to 30° C.

The reaction of a compound of the formula XI, leading to introduction of a leaving group of the formula LG2, with a leaving group forming agent LG*-X in which X is halogen, especially chloro, LG* is an electrophilic radical capable, with the hydroxy to which it is bound, of forming a leaving group LG2, especially a sulfonylhalogenide, preferably toluolsolfonylchloride, to yield a compound of the formula XII preferably takes place in the presence of a base, such as an alkali metal hydroxide, for example sodium hydroxide, in an aqueous organic solvent, such as an aqueous halogenated hydrocarbon, for example dichloromethane, at preferred temperatures in the range from 0 to 50° C., for example from 20 to 30° C.

The cyclization of a compound of the formula XII to a compound of the formula XIII under basic conditions in the presence of a phase transfer catalyst, for example a tetraalkylammonium halogenide, such as tetra-n-butylammoniumbromide, in the presence of a base, especially an alkali metal hydroxide, such as sodium hydroxide, in an aqueous organic solvent, such as an aqueous halogenated hydrocarbon, for example dichloromethane, at preferred temperatures in the range from 0 to 50° C., for example from 20 to 30° C.

The deprotection of a compound of the formula XIII preferably takes place with the acid $H_nA$ which is part of the salt of the resulting formula II in a polar solvent, such as an alcohol, for example an alkanol, such as ethanol or especially methanol, in the presence of an amine base, for example isopropylamine, at preferred temperatures in the range from 0 to 50° C., for example at 20 to 30° C.

The hydrogenation of a compound of the formula VIII* to a compound of the formula X* in the presence of a chiral hydrogenation catalyst (usually formed from a precatalyst, for example on Ruthenium(I) basis, such as Bis(norbornadiene)rhodium(I)tetrafluoroborate and a chiral ligand), for example as defined below, preferably takes place with hydrogen under elevated pressure, for example in the range of from 3 to 50 bar, such as 20 to 40 bar, in a polar solvent, especially and 2,2,2-trifluoroethanol, at temperatures preferably ranging from 30 to 80° C., for example from 40 to 60° C. This hydrogenation more generally takes place with hydrogen in the presence of a transition metal catalyst, preferably in the presence of a transition metal catalyst comprising an organometallic complex and a chiral ligand. The reduction may occur under hetero- or homogeneous hydrogenation conditions, preferably under homogeneous hydrogenation conditions. The transition metal is selected from group 9 or 10 of the periodic table. Therefore, the transition metal catalyst comprises, for example, Cobalt (Co), Rhodium (Rh), Iridium (Ir), Nickel (Ni), Palladium (Pd) and/or Platinum (Pt).

Among the chiral catalysts, all those allowing the hydrogenation of the double bond in the compound of formula VIII* to yield the configuration at the former double bond shown in formula X* are appropriate. It is further preferred that the chiral ligand comprises a chiral ferrocene.

A preferred chiral ferrocene has the formula:

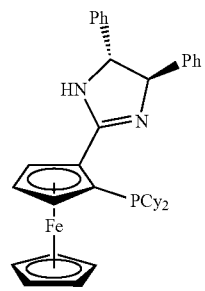

but others are possible as well, for example of any one of the following formulae:

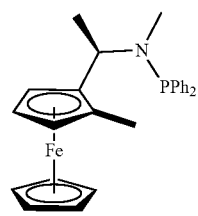

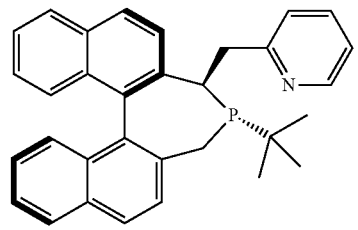

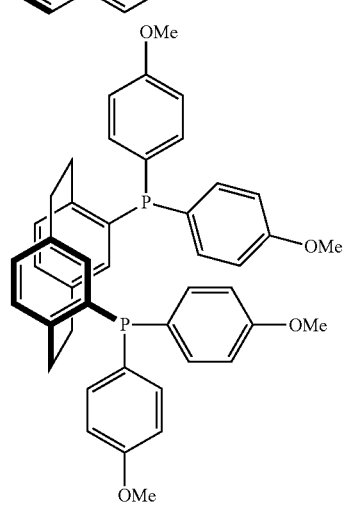

-continued

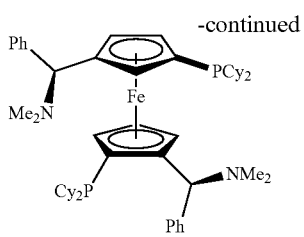

Mixtures of two or more such ligands, especially those defined by the formulae above, are also possible.

Usually, the active catalyst is formed by mixing 0.9 to 1.2, preferably 1.0 to 1.1, more preferably 1.0 to 1.05 mole of chiral ligand with 1.0 mole of transition metal atoms comprised in the transition metal catalyst. For example, if a dimer transition metal catalyst is employed, preferably two moles of chiral ligand are reacted with one mole of transition metal catalyst in order to form the "active catalyst".

The chiral ligand is typically added to the reaction mixture in a solution prepared with the same solvent used for the reaction.

The reduction of a compound of the formula X* to a compound of the formula XI* under ring opening preferably takes place in the presence of a complex hydride capable of reducing the lactone group in formula X to the open ring in formula XI with two hydroxy groups, such as lithium borohydride, in an aprotic solvent, such as a linear or preferably a cyclic ether, for example tetrahydrofurane, preferably at a temperature in the range from 0 to 50° C., for example at 20 to 30° C.

Amino protecting groups are preferably groups that can be cleaved by not too harsh acidic conditions, for example in the presence of a hydrogen halogenide, such as HCl, or in the case where a compound of formula II is the direct reaction product, an acid of the formula $H_nA$ as defined for a compound of the formula II, especially wherein n is 1 and A is a halogenide anion, especially a chloride anion. For example, 9-fluorenylmethoxycarbonyl, allyloxycarbonyl or especially tert-butoxycarbonyl.

The reaction of a compound of formula XI*, leading to introduction of a leaving group of the formula LG2, with a leaving group forming agent LG*-X in which X is halogen, especially chloro, LG* is an electrophilic radical capable, with the hydroxy to which it is (to be) bound, of forming a leaving group LG2, especially a sulfonylhalogenide, preferably toluolsolfonylchloride, to yield a compound of the formula XII* preferably takes place in the presence of a base, such as an alkali metal hydroxide, for example sodium hydroxide, in an aqueous organic solvent, such as an aqueous halogenated hydrocarbon, for example dichloromethane, at preferred temperatures in the range from 0 to 50° C., for example from 20 to 30° C.

The cyclization of a compound of formula XII* to a compound of the formula XIII* preferably takes place under basic conditions in the presence of a phase transfer catalyst, for example a tetraalkylammonium halogenide, such as tetra-n-butylammoniumbromide, in the presence of a base, especially an alkali metal hydroxide, such as sodium hydroxide, in an aqueous organic solvent, such as an aqueous halogenated hydrocarbon, for example dichloromethane, at preferred temperatures in the range from 0 to 50° C., for example from 20 to 30° C.

The deprotection of a compound of the formula XIII* preferably takes place with the acid $H_nA$ which is part of the salt of the resulting formula II in a polar solvent, such as an alcohol, for example an alkanol, such as ethanol or especially methanol, at preferably elevated temperatures in the range from 50 to 120° C., for example at 100 to 115° C.

The compound of the formula III, in a further single invention embodiment or as part of the total synthesis of a compound of the formula I according to invention, is according to one embodiment preferably obtained by halogenating a compound of the formula XVIII:

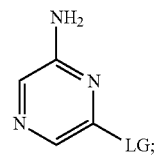

(XVIII)

in which LG is a leaving group, especially halogeno, such as chloro, with a halogenating agent to yield a compound of the formula XIX.

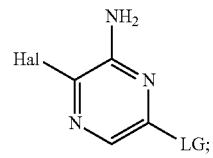

(XIX)

in which LG is a leaving group, especially as just defined, and Hal is halogen, especially chloro.

The reaction preferably takes place with an halo-succinimide, such as bromosuccinimide, so that preferably Hal is bromo. The reaction takes place in one or more aprotic solvents such as dichloromethane, acetonitrile, tetrahydrofurane, N,N-dimethylacetamide or the like, preferably in the temperature range of 20° C.~100° C.

The compound of the formula XIX can then or first be substituted with a mercapto compound of the formula XX:

$$R_6O-C(=O)-CH_2-CH_2-SH \quad (XX);$$

wherein $R_6$ is unsubstituted or substituted alkyl or unsubstituted or substituted aryl, especially $C_1$-$C_6$alkyl, such as ethyl, to give a compound of the formula XXI:

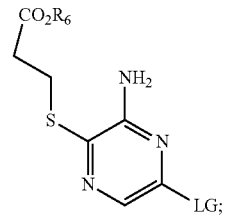

(XXI)

wherein LG is a leaving group and $R_6$ is unsubstituted or substituted alkyl or unsubstituted or substituted aryl, especially as just defined.

The reaction preferably takes place in the presence of a noble metal complex comprising a noble metal, especially Palladium, and a ligand, such as Xantphos, in the presence of a tertiary amine, such as diisopropylethylamine, in an aprotic solvent, for example an ester, preferably a cyclic ester, such as dioxane, at preferably elevated temperatures, for example from 30° C. to the boiling point of the reaction mixture.

In a further sole or combined embodiment, the compound of the formula XXI is then treated with an alkoxylate, especially a methoxylate or an ethoxylate, of an alkaline metal, especially lithium, potassium or most especially sodium, to yield a compound of the formula XXII:

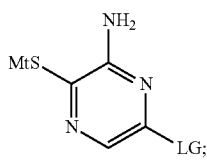

(XXII)

wherein Mt is an alkaline metal, especially sodium. This reaction preferably takes place in a solvent, such as a mixture of an alcohol, for example methanol or ethanol (especially an alcohol matching with the alkoxylate so that the alkoxygroup is identical to the organic rest in the alcohol, and an ether, for example a cyclic ether, such as tetrahydrofurane, preferably at a temperature in the range from 0 to 50° C.

The compound of the formula XXII is then reacted with a compound of the formula XXIII:

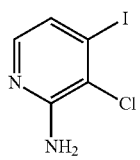

(XXIII)

to yield the compound of the formula III:

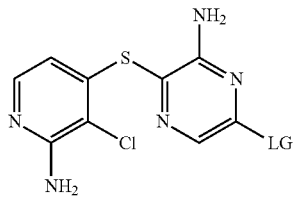

III wherein LG is a leaving group, especially as defined above for a compound of the formula III.

The reaction preferably takes place in the presence of a noble metal complex, especially formed from $Pd_2(dbba)_2$, in the presence of a ligand, such as Xantphos, and of a tertiary nitrogen base, such as diisopropylamine, in an aprotic solvent, such as an ether, for example a cyclic ether, especially dioxane, at preferably elevated temperatures, for example in the range from 30° C. to the boiling point of the reaction mixture.

The compound of formula XXIII can preferably be obtained by reacting a compound of the formula XXIV:

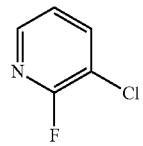

(XXIV)

with iodine in the presence of a strong base.

This reaction preferably takes place in the presence of a strong base, especially an alkyl-alkaline metal, such as n-butylllithium, and a nitrogen base, especially di-isopropylamine or diethylamine, in a solvent, such as an acyclic or especially cyclic ether, preferably tetrahyrofurane, at preferably low temperatures, for example in the range from –80 to –5° C.

This results in a compound of the formula XXV:

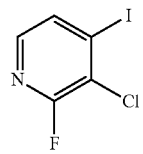

(XXV)

which is then treated with ammonia to yield the compound of the formula XXIII.

This reaction then preferably takes place in the presence of gaseous ammonia and an inert polar solvent, such as DMSO, especially at elevated temperatures, preferably in the range from 30° C. to the boiling point of the reaction mixture, for example at 85 to 95° C.

As a preferred alternative to the synthesis from a compound of the formula XVIII, a compound of the formula XIX in which Hal is chloro and LG is as defined above preferably can also be obtained by treating a compound of the formula XXVI:

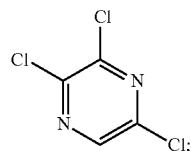

(XXVI)

with ammonia to yield the compound of the formula XIX in which Hal is chloro chloro (the reaction conditions are preferably as just described for the reaction of the compound of the formula XXV) and then employing the further reactions via compounds of the formula XXI, XXII and XXIII above to the compound of the formula III, each as defined above.

In a further and most preferred embodiment, a compound of the formula XXVI just described is reacted with ammonia (preferably in an aqueous medium ant at temperatures in the range from 0 to 80° C.) to yield the compound of the formula XIX in which Hal is halo, preferably chloro, which is then reacted with a (preferably anhydrous) alkaline metal sulfide of the formula $Mt_2S$, in which Mt is an alkaline metal, especially sodium, and then with a quaternary ammonium halogenide of the formula $(alk)_4NZ$, in which each alk is independently of the others alkyl, especially n-alkyl, such as $C_1$-$C_6$-alkyl and Z is halo, especially chloro or more especially bromo, to yield a compound of the formula XXVII:

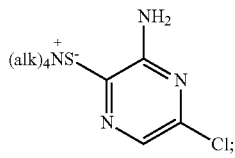

(XXVII)

in which alk is independently of the others alkyl, especially n-alkyl, such as $C_1$-$C_6$-alkyl, which can then be reacted with a compound of the formula XXIII (which can preferably be prepared as described above)), preferably in the presence of a copper(I) iodide complex, such as CuI/phenanthroline, in an appropriate solvent, for example in water or an alcohol or a mixture thereof, preferably in water and/or methanol, ethanol or especially isopropanol, preferably at temperatures in the range from −20 to 80° C., for example from 0 to 40° C., to yield the compound of the formula III.

In another embodiment is a method for the manufacture of a compound of Formula I, or a pharmaceutically acceptable salt, acid co-crystal, hydrate or other solvate thereof, said method comprising reacting a compound of formula II with a compound of formula III according to the following reaction scheme:

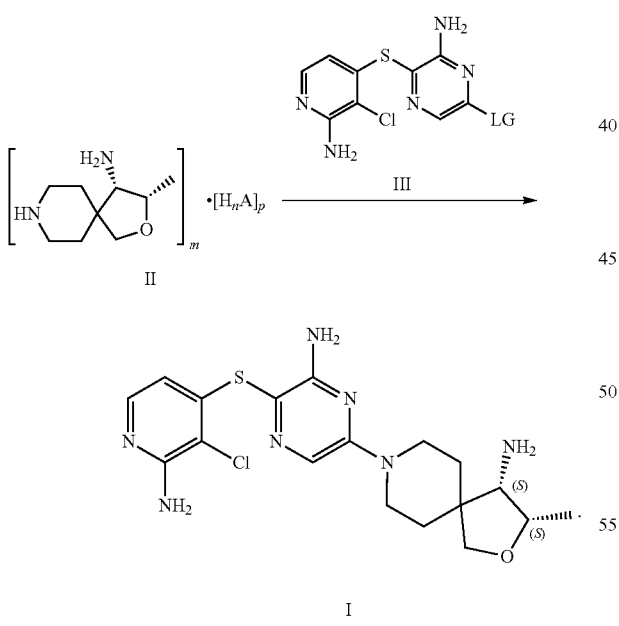

wherein LG is a leaving group, A is the anion of a protic acid, and n, m and p are independently 1, 2 or 3, so that the salt of the formula II is electrically neutral.

In a further embodiment, is a method where the compound of formula II is obtained either (i) by deprotecting or (ii) by reducing a compound of the formula IV,

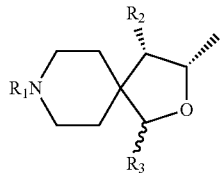

IV wherein in case (i) $R_1$ is a secondary amino protecting group and $R_2$ is a protected amino group and $R_3$ is hydrogen, or in case (ii) $R_1$ is a secondary amino protecting group, $R_2$ is amino and $R_3$ is hydroxyl, and if required reacting the resulting compound of the formula IVa:

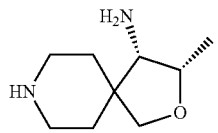

IVa with an acid of the formula $H_nA$ to yield the compound of formula II.

In a further embodiment is a method for the manufacture of a compound of formula II comprising reacting a compound of the formula V:

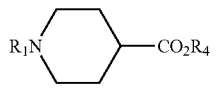

V wherein $R_1$ is a secondary amino protecting group and $R_4$ is a carboxyl (—COOH) protecting group, in the presence of a strong base with L lactide of the formula:

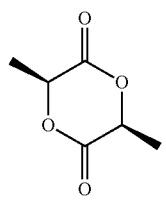

to yield a compound of the formula VI:

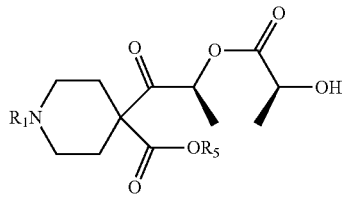

VI wherein $R_1$ is a secondary amino protecting group and $R_5$ is an unsubstituted or substituted alkyl, unsubstituted or substituted cycloalkyl or unsubstituted or substituted aryl; or alternatively yielding a compound of the formula VI*:

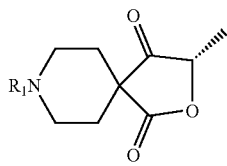
VI* wherein R₁ is a secondary amino protecting group.

In a further embodiment, the method further comprises cyclizing a compound of the formula VI:

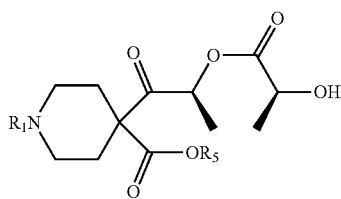
VI wherein R₁ a secondary amino protecting group and R₅ is unsubstituted or substituted alkyl, unsubstituted or substituted cycloalkyl or unsubstituted or substituted aryl, with hydroxylamine, of a salt thereof; or alternatively comprising cyclizing a compound of the formula VI*:

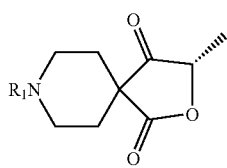
VI* wherein R₁ is a secondary amino protecting group, to yield a compound of the formula VII:

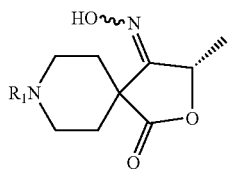
VII wherein R₁ a secondary amino protecting group.

In a further embodiment, the method further comprises either: (a-i) hydrogenating a compound of the formula VII:

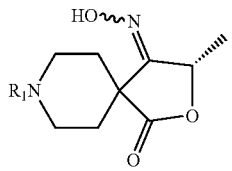
VII wherein R₁ a secondary amino protecting group, to yield an amino compound of the formula VIII:

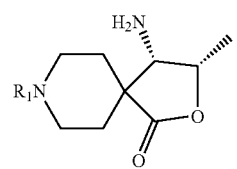
VIII wherein R₁ is a secondary amino protecting group; or (a-ii) acylating said compound of the formula VII under reducing conditions to yield a compound of the formula VIII*:

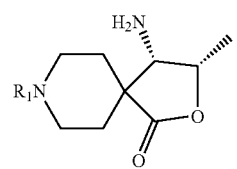
VIII* wherein R₁ is a secondary amino protecting group and *R₂ is an acylated amino.

In a further embodiment, the method further comprises reducing a compound of the formula VII:

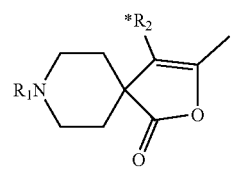
VII wherein R₁ a secondary amino protecting group; which compound is a compound of the formula IV of claim 2 wherein R₁ is a secondary amino protecting group, R₂ is amino and R₃ is hydroxyl; to a compound of the formula IX:

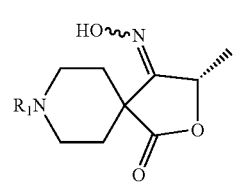
IX wherein R₁ is a secondary amino protecting group, which compound is a compound of the formula IV wherein R₁ is a secondary amino protecting group, R₂ is amino and R₃ is hydroxyl; then using reducing step (ii) according to claim 2 for a compound of the corresponding formula IV falling under formula IX using a trialkylsilane to yield a compound of the formula II as defined in claim 1 or a compound of the formula V:

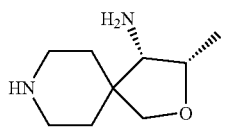

V which is then converted to the compound of formula II by treating with an acid of the formula $H_nA$ wherein A is an acid anion and n is an integer.

In a further embodiment, the method comprises reacting an amino compound of formula VIII:

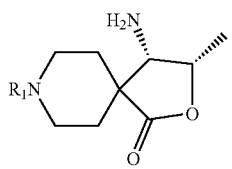

VIII wherein $R_1$ is a secondary amino protecting group; with an amino protecting group to yield a compound of formula X:

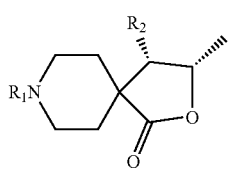

X wherein $R_1$ is a secondary amino protecting group and $R_2$ is a protected amino group.

In a further embodiment, the method further comprises reducing a compound of formula X:

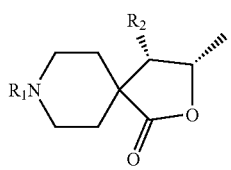

X wherein $R_1$ is a secondary amino protecting group and $R_2$ is a protected amino group to a compound of the formula XI:

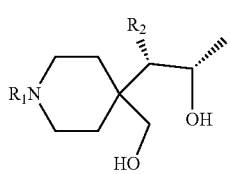

XI wherein $R_1$ is a secondary amino protecting group and $R_2$ is a protected amino group; which compound of formula XI is reacted at the hydroxy of the hydroxymethyl group with a leaving group forming agent of the formula LG*-X in which LG* is an electrophilic radical capable, with the hydroxy to which it is bound, of forming a leaving group LG2 and X is halogen, to yield a compound of the formula XII:

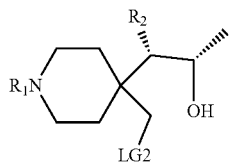

XII wherein $R_1$ is a secondary amino protecting group, $R_2$ is a protected amino group and LG2 is a leaving group; which compound of formula XII is then cyclized under basic conditions to yield a compound of the formula XIII:

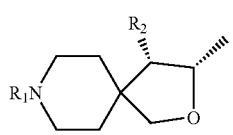

XIII wherein $R_1$ is a secondary amino protecting group and $R_2$ is a protected amino group; wherein the deprotecting step (i) of claim 2 for a compound of formula IV of the compound of formula XIII is conducted using an acid $H_nA$.

In a further embodiment, the method further comprises hydrogenating a compound of formula VIII*:

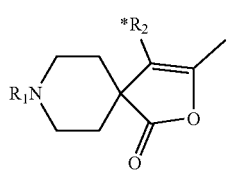

VIII* wherein $R_1$ is a secondary amino protecting group and *$R_2$ is an acylated amino; in the presence of a chiral hydrogenation catalyst to yield a compound of the formula X*:

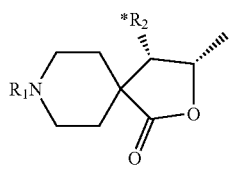

X* wherein $R_1$ is a secondary amino protecting group and *$R_2$ is an acylated amino group; which compound of formula X* is reduced to a compound of the formula XI*:

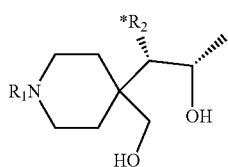

wherein R₁ is a secondary amino protecting group and *R₂ is an acylated amino group; which compound of formula XI* is reacted at the hydroxy of the hydroxymethyl group with a leaving group forming agent of the formula LG*-X in which LG* is an electrophilic radical capable of forming, with the hydroxy to which it is bound, a leaving group LG2 and X is halogen, to yield a compound of the formula XII*:

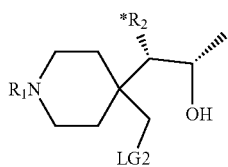

wherein R₁ is a secondary amino protecting group, R₂ is a protected amino group and LG2 is a leaving group; which compound of formula XII* is cyclized under basic conditions to yield a compound of the formula XIII*:

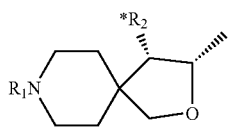

in which R₁ is a secondary amino protecting group and *R₂ is an acylated amino group; where the deprotecting/deacylating step (i) for a compound of the corresponding formula IV in claim 2 of the compound of formula XIII* is conducted using an acid KA.

In another embodiment is the manufacture of a compound of the formula III:

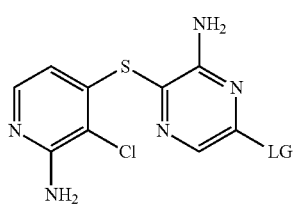

wherein LG is a leaving group, comprising first obtaining a compound of the formula XIX:

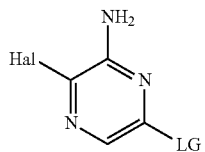

in which LG is chloro and Hal is chloro, by treating a compound of the formula XXVI:

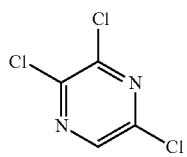

with ammonia to yield the compound of formula XIX; then reacting the compound of the formula XIX with an alkaline metal sulfide of the formula Mt₂S, in which Mt is an alkaline metal and then with a quaternary ammonium halogenide of the formula (alk)₄NZ, in which each alk is independently of the others alkyl, and Z is halo, to yield a compound of the formula XXVII:

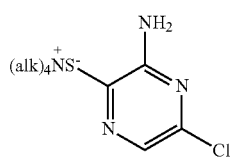

in which each alk is independently alkyl, which is then reacted with a compound of the formula XXIII:

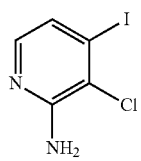

to yield the compound of the formula III.

In a further embodiment of the method, the Mt alkyline metal is sodium.

In another embodiment, is a compound selected from the group consisting of:

(i) a salt compound of the formula II:

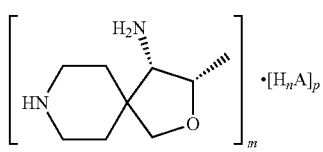

wherein A is the anion of a protic acid and n, m and p are selected from 1, 2 and 3, so that the salt of the formula II is electrically neutral; (ii) a compound of the formula VI:

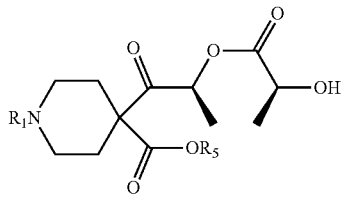

wherein $R_1$ is a secondary amino protecting group and $R_5$ is unsubstituted or substituted alkyl, unsubstituted or substituted cycloalkyl or unsubstituted or substituted aryl;

(iii) a compound of the formula VI*:

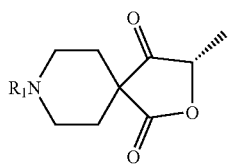

wherein $R_1$ is a secondary amino protecting group; (iv) a compound of the formula VII:

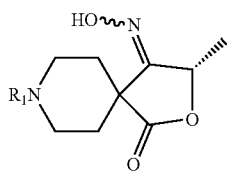

wherein $R_1$ is a secondary amino protecting group; (v) a compound of the formula VIII:

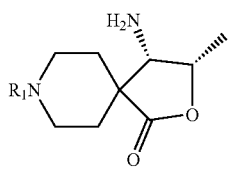

wherein $R_1$ is a secondary amino protecting group; (vi) a compound of the formula IX:

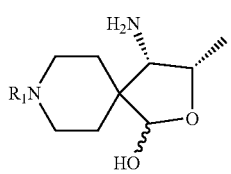

wherein $R_1$ is a secondary amino protecting group; (vii) a compound of the formula VIII*:

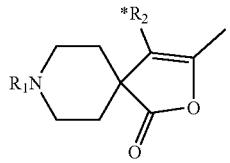

wherein $R_1$ is a secondary amino protecting group and *$R_2$ is an acylated amino; (viii) a compound of the formula X*:

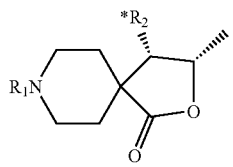

wherein $R_1$ is a secondary amino protecting group and *$R_2$ is an acylated amino; (ix) a compound of the formula XI*:

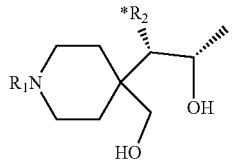

wherein $R_1$ is a secondary amino protecting group and *$R_2$ is an acylated amino; (x) a compound of the formula XII*:

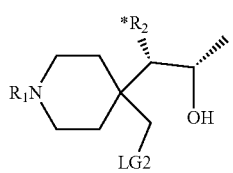

wherein $R_1$ is a secondary amino protecting group, *$R_2$ is an acylated amino group and LG2 is a leaving group; (xi) a compound of the formula XIII*:

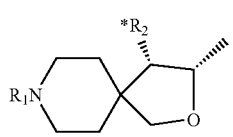

in which $R_1$ is a secondary amino protecting group and *$R_2$ is an acylated amino group; (xii) a compound of the formula X:

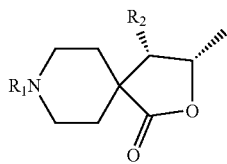

wherein $R_1$ is a secondary amino protecting group and $R_2$ is a protected amino group; (xiii) a compound of the formula XI:

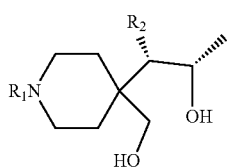

wherein $R_1$ is a secondary amino protecting group and $R_2$ is a protected amino group; (xiv) a compound of the formula XII:

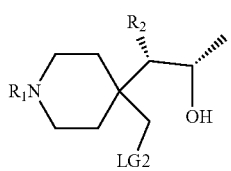

wherein $R_1$ is a secondary amino protecting group, $R_2$ is a protected amino group and LG2 is a leaving group; and (xv) a compound of the formula XIII:

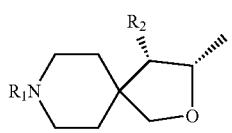

wherein $R_1$ is a secondary amino protecting group and $R_2$ is a protected amino group; or a salt thereof.

In a further embodiment, A is Cl.
In a further embodiment, $R_1$ is tert-butoxycarbonyl.

EXAMPLES

The following examples serve to illustrate the invention without limiting the scope otherwise defined herein. Abbreviations used: Ac (acetate); AcOH (acetic acid); Ac$_2$O (aceticanhydride); Boc (tert-butoxycarbonyl); Boc$_2$O (Di-tert-butyl dicarbonate); Brine (sodium chloride solution saturated at RT); n-Bu$_4$NBr (Tetra-(n-butyl)ammonium bromide); n-BuLi (n-Butyllithium); calcd (calculated); DCM (dichloromethane); DIBAL-H (Diisobutylaluminiumhydride); DIPEA (Di(isopropyl)ethylamine); DMAc (dimethyl acetamide); DMSO (dimethyl sulfoxide); DMSO-d$_6$ (per-deuterated dimethyl sulfoxide); eq or equiv. (equivalents); Et (Ethyl); EtOAc (ethyl acetate); HRMS (High Resolution Mass Spectroscopy); hrs. (Hour(s)); IPA (Isopropylamine); IT (Internal Temperatur (of a reaction mixture)); LOQ (Limit of Quantification); MCC (Microcrystalline Cellulose); Me (Methyl); MeOH (Methanol); MTBE (methyl tertiary-butyl ether); NMR (Nuclear Magnetic Resonance); $^i$PrOH (Isopropanpol); $^i$Pr$_2$NH (diisopropyl amine); Rt or RT (Room Temperature (about 20 to 25° C.)); TBAB (Tetra-(n-butyl)ammoniumbromide); Tf-OH (triflic acid); THF (Tetrahydrofurane); TsCl (Tosylchloride); Triflic acid (Trifluoromethane sulfonic acid); and Xantphos (4,5-Bis (diphenylphosphino)-9,9-dimethylxanthene).

Experimental procedures: three basic procedures (corresponding to Example 1=Route B); Example 2=Route C; and Example 3=Route D) are outlined in the following reaction overview schemes:

Example 1

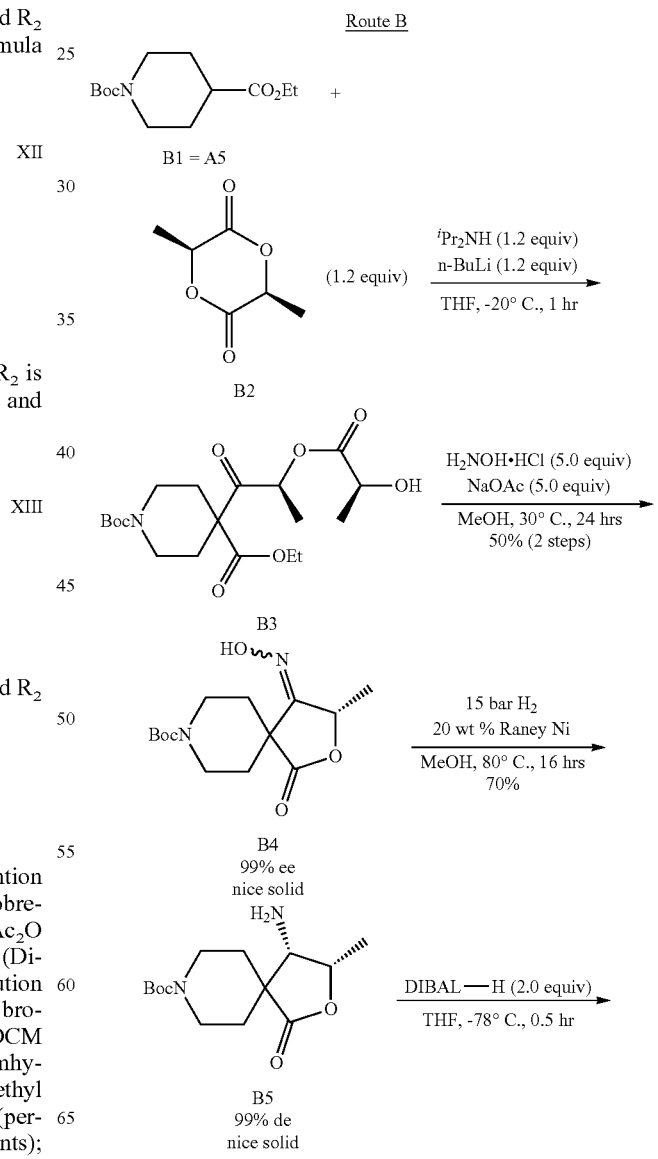

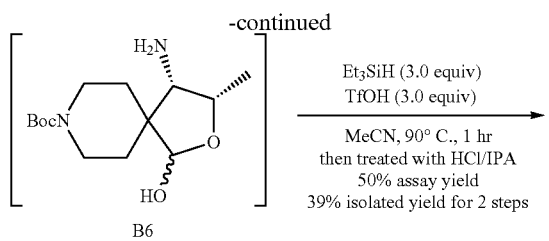

filtrate was concentrated to dryness to give B3 as a pale yellow oil (36.0 g, 71 wt %, 81% assay yield), which was used in the next step without further purification. $^1$H NMR (400 MHz, CDCl$_3$) δ=5.42 (q, J=6.8 Hz, 1H), 4.36-4.27 (m, 1H), 4.27-4.16 (m, 2H), 3.71-3.49 (m, 2H), 3.39-3.24 (m, 2H), 2.81 (br d, J=5.0 Hz, 1H), 2.24-1.81 (m, 4H), 1.44 (s, 15H), 1.27 (t, J=7.1 Hz, 3H).

Step b

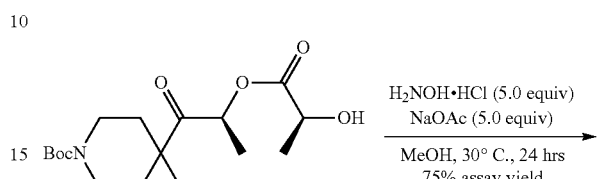

Step a

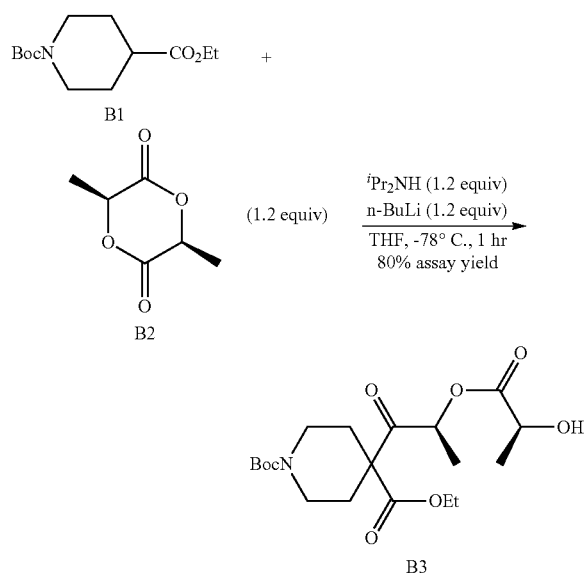

A 500 mL three-necked round bottomed flask A under an nitrogen atmosphere was charged with diisopropylamine (9.44 g, 93.3 mmol, 1.2 eq) and THF (200 mL). The solution was cooled to an IT=−20° C., 2.4 M. n-BuLi in hexanes (38.9 mL, 1.2 eq) was added dropwise during 30 min. The reaction was stirred at −20° C. for 30 min and then cooled to −70° C. A solution of 1-(tert-butyl) 4-ethyl piperidine-1, 4-dicarboxylate (Jinan Welt Chem. Co., Ltd., Jinan, China) (20.0 g, 77.7 mmol, 1.0 eq) in THF (20 mL) was added dropwise during 30 min while maintaining the IT=−70° C. to −60° C. The reaction was stirred at −70° C. for 30 min and a pale yellow solution was obtained.

A 500 mL three-necked round bottomed flask B under an nitrogen atmosphere was charged with L-lactide (13.4 g, 93.3 mmol, 1.2 eq) and THF (120 mL). The solution was cooled to an IT=−70° C. The solution in flask A was transferred slowly to flask B via cannula during 30 min while maintaining the IT=−70° C. to −60° C. The reaction was stirred at −70° C. for 30 min. The reaction solution was transferred to flask C containing 3% HCl (300 mL) via cannula during 30 min while maintaining the IT=0° C. to 5° C. The mixture was extracted with EtOAc (400 mL×2) and washed with 20 wt % brine (200 mL). The organic layer was separated, dried over anhydrous Na$_2$SO$_4$ and filtered. The To a 250 mL round bottomed flask was added: the above yellow oil (15.0 g, 71 wt %, 26.5 mmol), hydroxylamine hydrochloride (9.3 g, 132.6 mmol, 5.0 eq), sodium acetate (10.9 g, 132.6 mmol, 5.0 eq) and methanol (150 mL). The mixture was stirred for 24 hrs at 20-25° C. The resulting suspension was filtered through MCC and the filter cake was washed with MeOH (20 mL×2). The filtrate was concentrated to ca. 60 mL, water (60 mL) was then added dropwise during 15 min, a white solid precipitated out. The suspension was stirred overnight and filtered. The filter cake was washed with a mixture of MeOH (5 mL) and water (25 mL) and dried under vacuum to give B4 as a white solid (4.9 g, 59%). $^1$H NMR (400 MHz, DMSO-d$_6$) δ=11.45 (s, 1H), 5.33 (q, J=6.6 Hz, 1H), 3.73-3.58 (m, 2H), 3.56-3.43 (m, 1H), 3.43-3.35 (m, 1H), 1.87-1.65 (m, 4H), 1.52 (d, J=6.7 Hz, 3H), 1.41 (s, 9H).

Step c

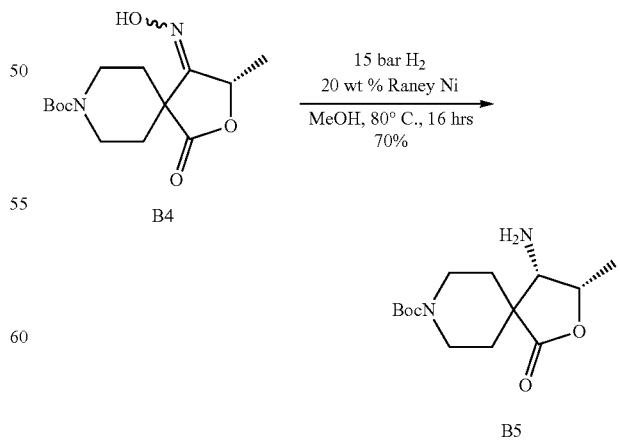

To a 1 L reactor with an impeller stirrer under an nitrogen atmosphere was added Raney-Ni (5 g) and MeOH (250 mL), followed by tert-butyl (S)-4-(hydroxyimino)-3-methyl-1-oxo-2-oxa-8-azaspiro[4.5]decane-8-carboxylate B4 (25.0 g, 83.80 mmol). The reactor was purged with nitrogen three times and then with hydrogen three times. The mixture was stirred for 16 hrs under a hydrogen pressure of 20 bar at IT=80° C. The reaction mixture was filtered through microcrystalline cellulose and the filter cake was washed with MeOH (10 ml). The filtrate was concentrated to dryness to give a white solid (23.0 g). EtOAc (220 mL) was added to the solid, the resulting suspension was heated to reflux (JT=100° C.) and n-heptane (550 mL) was added portionwise. The resulting clear solution was cooled to rt during 2 hrs and left standing overnight to give B5 as a colorless crystalline product (16.7 g, cis/trans>9911, 70%). ¹H NMR (400 MHz, CDCl₃) δ=4.75-4.64 (m, 1H), 3.89-3.80 (m, 1H), 3.68-3.58 (m, 1H), 3.48-3.33 (m, 3H), 1.92-1.61 (m, 4H), 1.46 (s, 9H), 1.40 (d, J=6.5 Hz, 3H).

Step d

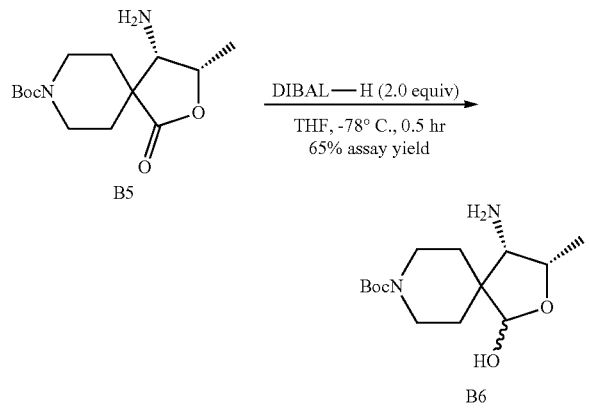

A 500 mL three-necked round bottomed flask under an nitrogen atmosphere was charged with tert-butyl (3S,4S)-4-amino-3-methyl-1-oxo-2-oxa-8-azaspiro[4.5]decane-8-carboxylate B5 (6.0 g, 21.1 mmol) and THF (200 mL). The solution was cooled to an IT=−78° C., 1.0 M DIBAL (42.2 mL, 42.2 mmol, 2.0 eq) was added dropwise during 30 min. The reaction was stirred at −78° C. for 30 min. A saturated aqueous Na,K-tartrate solution (150 mL) was added carefully to quench the reaction while maintaining the IT=−78° C. to −60° C. The mixture was stirred vigorously at 20-25° C. until two clear phases were obtained (ca. 1.5 hrs) and extracted with EtOAc (200 mL×2). The combined organic extracts were washed with 20 wt % brine (200 mL), dried over Na₂SO₄, filtered and concentrated to give B6 as a viscous oil (6.1 g, 64 wt %, 65% assay yield), which was used in the next step without further purification. ¹H NMR (400 MHz, CDCl₃) δ=5.06 (s, 1H), 4.39-4.29 (m, 1H), 3.68-3.57 (m, 2H), 3.35-3.24 (m, 2H), 3.18 (d, J=4.4 Hz, 1H), 1.98-1.85 (m, 1H), 1.75-1.54 (m, 3H), 1.46 (s, 9H), 1.35 (d, J=6.6 Hz, 3H).

Step e

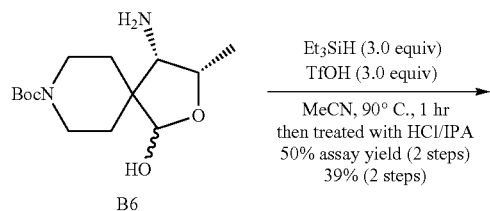

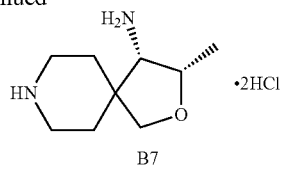

B7

To a 100 mL round bottomed flask was added 6.0 g of the above viscous oil and acetonitrile (150 mL). The flask was cooled in an ice-water bath and triethylsilane (7.4 g, 63.3 mmol), triflic acid (9.5 g, 63.3 mmol) was added subsequently. The reaction was then stirred for 1 hr in a 90° C. oil bath. The reaction was then cooled to 20-25° C. and poured into a separation funnel and washed with n-heptane (100 mL×2). The acetonitrile layer was separated and concentrated to dryness to give a colorless oil, which was diluted in EtOAc (150 mL). 6N HCl in isopropanol (30 mL) was added dropwise with stirring, white solid precipitated out. MTBE (150 mL) was added and the white suspension was stirred for 2 hrs and filtered. The filter cake was washed with EtOAc (50 mL×2) to give a white solid, which was dissolved in MeOH (6.0 mL), EtOAc (18 mL) was added dropwise with stirring. The resulting white suspension was filtered and washed with EtOAc (10 mL×2) to give B7 as a white solid (2.5 g, 81 wt %, 39% over two steps). ¹H NMR (400 MHz, DMSO-d₆) δ=9.37 (br s, 1H), 9.25 (br s, 1H), 8.42 (br s, 3H), 4.26-4.17 (m, 1H), 3.72 (AB q, J=9.1 Hz, 2H), 3.50-3.41 (m, 1H), 3.28-3.18 (m, 1H), 3.18-3.09 (m, 1H), 2.99-2.74 (m, 2H), 2.07-1.63 (m, 4H), 1.22 (d, J=6.5 Hz, 3H).

Step f

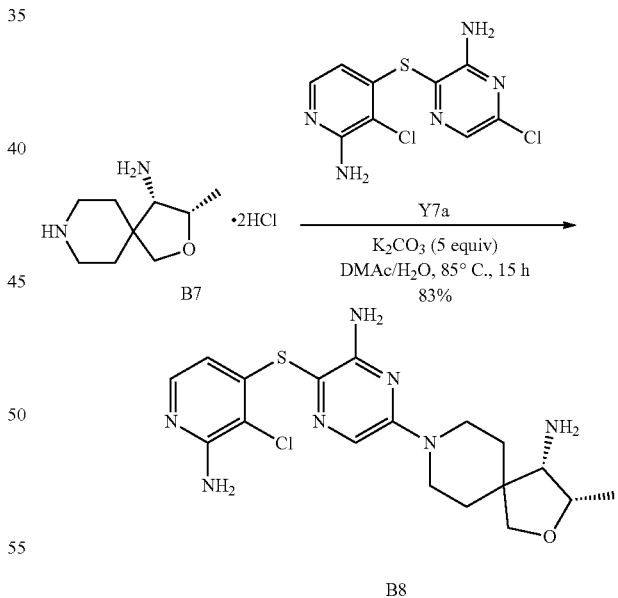

To a 10 mL Schlenk tube was added 3-((2-amino-3-chloropyridin-4-yl)thio)-6-chloropyrazin-2-amine Y7a (0.1 g, 0.347 mmol), (3S,4S)-3-methyl-2-oxa-8-azaspiro[4.5]decan-4-amine dihydrochloride B7 (0.1 g, 0.416 mmol, 1.2 eq), DMAc (0.6 mL) and 36 wt % aq. K₂CO₃ (0.66 g, 1.735 mmol, 5.0 eq). The mixture was stirred for 16 hrs in a 100° C. oil bath and cooled to 20-25° C. 20 wt % Brine (10 mL) was added and the mixture was extracted with EtOAc (20 mL×2). The combined extracts were washed with 20 wt %

Brine (10 mL×4), dried over anhydrous $Na_2SO_4$ and filtered. The filtrate was concentrated to dryness to give B8 as a yellow solid (121 mg, 83%). $^1$H NMR (400 MHz, DMSO-$d_6$) δ=7.64 (d, J=6.2 Hz, 1H), 7.62 (s, 1H), 6.26 (s, 2H), 6.13 (s, 2H), 5.74 (d, J=5.3 Hz, 1H), 4.12-4.02 (m, 1H), 3.90-3.78 (m, 2H), 3.67 (d, J=8.4 Hz, 1H), 3.49 (d, J=8.4 Hz, 1H), 3.33 (s, 2H), 2.91 (d, J=5.1 Hz, 1H), 1.78-1.68 (m, 1H), 1.67-1.57 (m, 1H), 1.56-1.41 (m, 2H), 1.08 (d, J=6.5 Hz, 3H).
Example 2
Route C
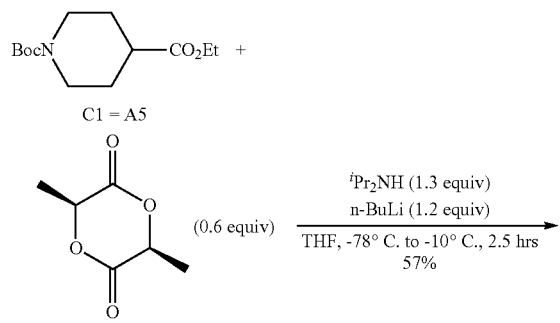
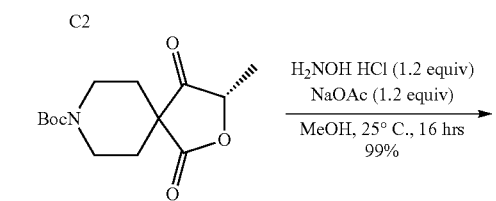
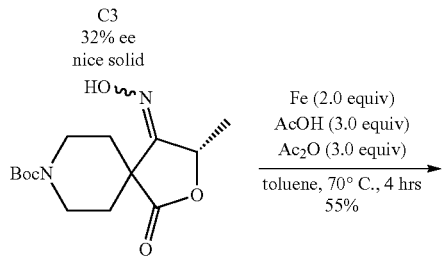
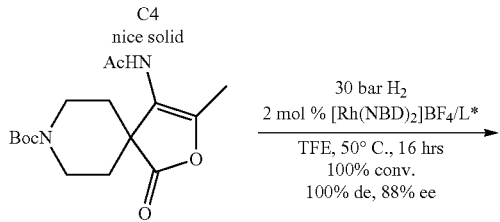
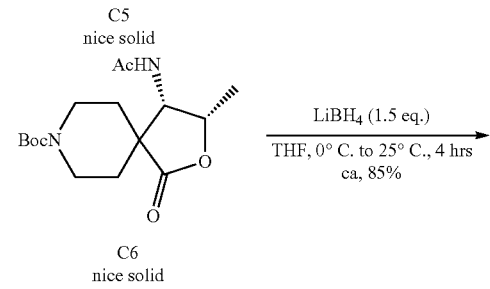
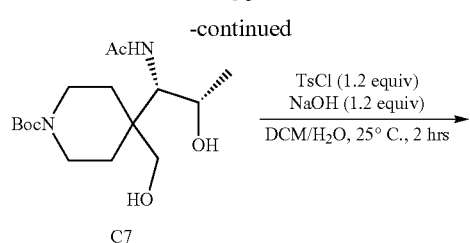
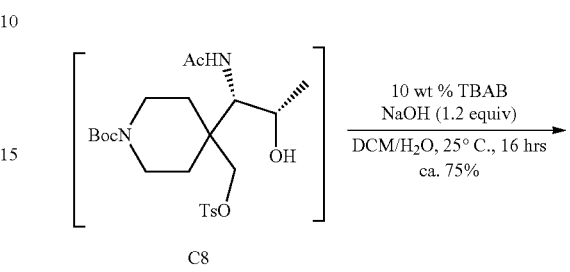
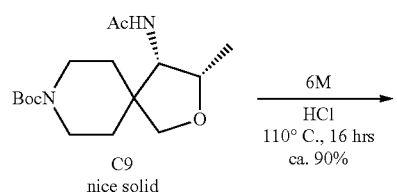
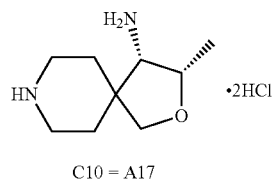
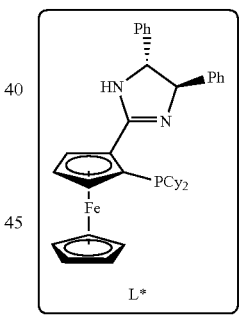
Step a:
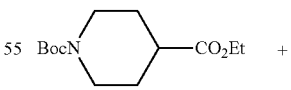
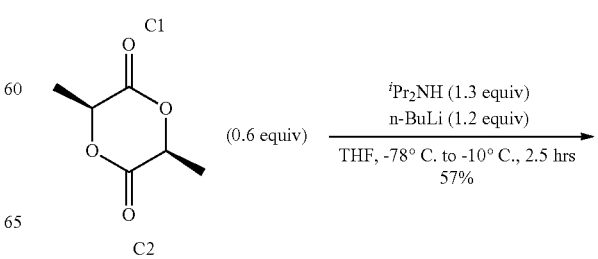

-continued

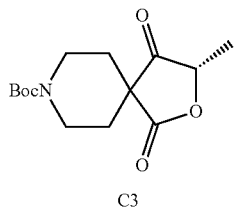

C3

A 1 L three-necked round bottomed flask A under an nitrogen atmosphere was charged with diisopropylamine (10.2 g, 100.8 mmol) and THF (200 mL). The solution was cooled to an IT=−20° C., 2.5 M n-BuLi in hexanes (37.3 mL, 93.3 mmol) was added dropwise during 30 min. The reaction was stirred at −20° C. for 30 min and then cooled to −70° C. A solution of 1-(tert-butyl) 4-ethyl piperidine-1,4-dicarboxylate (20.0 g, 77.7 mmol) in THF (30 mL) was added dropwise during 30 min while maintaining the IT=−70° C. to −60° C. The reaction was stirred at −70° C. for 1 h and a pale yellow solution was obtained. A solution of L-lactide (13.4 g, 93.3 mmol, 1.2 eq) in THF (50 mL) was added dropwise during 30 min while maintaining the IT=−70° C. to −60° C. The reaction was stirred at −70° C. for 1 h.

A 500 mL three-necked round bottomed flask B under an nitrogen atmosphere was charged with diisopropylamine (9.2 g, 90.9 mmol) and THF (180 mL). The solution was cooled to an IT=−20° C., 2.5 M n-BuLi in hexanes (33.6 mL, 84.0 mmol) was added dropwise during 30 min. The reaction was stirred at −20° C. for 30 min and then cooled to −70° C. A solution of 1-(tert-butyl) 4-ethyl piperidine-1,4-dicarboxylate (18.0 g, 70.0 mmol) in THF (27 mL) was added dropwise during 30 min while maintaining the IT=−70° C. to −60° C. The reaction was stirred at −70° C. for 1 h.

The solution in flask B was transferred slowly to flask A via cannula during 30 min while maintaining the IT=−70° C. to −60° C. The reaction was stirred at −70° C. for 1 h. Then the reaction was gradually warmed to −10° C. over 1 h and stirred at −10° C. for 30 min. The reaction solution was transferred to flask C containing 3% HCl (500 mL) via cannula during 30 min while maintaining the IT=0° C. to 5° C. The mixture was extracted with EtOAc (300 mL×2) and washed with 20 wt % brine (200 mL). The organic layer was separated, dried over anhydrous Na₂SO₄ and filtered. The filtrate was concentrated to dryness to give a colorless oil, which gradually solidified upon standing overnight. The solid was recrystallized from n-heptane/EtOAc to give C3 as a white solid (24.0 g, 57%). ¹H NMR (400 MHz, CDCl₃) δ=4.83 (q, J=7.0 Hz, 1H), 3.78-3.62 (m, 4H), 1.90-1.72 (m, 4H), 1.53 (d, J=7.1 Hz, 3H), 1.47 (s, 9H).

Step b

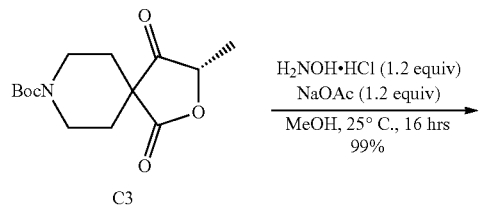

H₂NOH·HCl (1.2 equiv)
NaOAc (1.2 equiv)
─────────────────
MeOH, 25° C., 16 hrs
99%

-continued

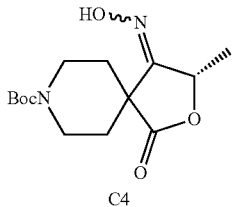

C4

To a 500 mL round bottomed flask was added tert-butyl (S)-3-methyl-1,4-dioxo-2-oxa-8-azaspiro[4.5]decane-8-carboxylate C3 (26.5 g, 93.5 mmol, 1.0 eq), hydroxylamine hydrochloride (7.8 g, 112.2 mmol, 1.2 eq), sodium acetate (9.2 g, 112.2 mmol, 1.2 eq) and methanol (200 mL). The mixture was stirred overnight at 20-25° C. The reaction mixture was concentrated to dryness and the resulting solid was diluted in EtOAc (300 mL), and washed with water (200 mL) and 20 wt % brine (200 mL). The organic phase was dried over Na₂SO₄, filtered, and concentrated to dryness to give C4 as a white solid (27.9 g, 99%, partially racemised). ¹H NMR (400 MHz, DMSO-d₆) δ=11.45 (s, 1H), 5.33 (q, J=6.6 Hz, 1H), 3.73-3.58 (m, 2H), 3.56-3.43 (m, 1H), 3.43-3.35 (m, 1H), 1.87-1.65 (m, 4H), 1.52 (d, J=6.7 Hz, 3H), 1.41 (s, 9H).

Step c

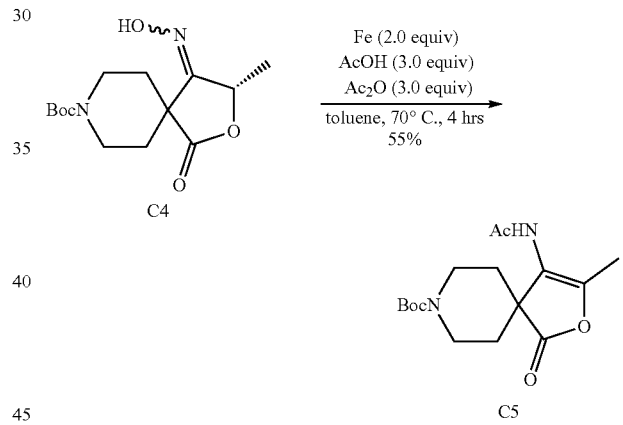

To a 500 mL round bottomed flask under a nitrogen atmosphere was added subsequently tert-butyl-4-(hydroxyimino)-3-methyl-1-oxo-2-oxa-8-azaspiro[4.5]decane-8-carboxylate C4 (27.9 g, 93.5 mol), toluene (150 mL), acetic anhydride (29.1 g, 280.6 mmol), acetic acid (16.8 g, 280.6 mmol) and iron (10.4 g, 187.0 mmol). The mixture was stirred vigorously for 4 hrs in a 70° C. oil bath and cooled to rt. The suspension was filtered through microcrystalline cellulose to remove solid residue, which was then washed with EtOAc (150 mL×2). The combined filtrates were cooled in an ice-water bath and washed with 5 wt % NaHCO₃ (300 mL) and 20 wt % brine (300 mL). The organic layer was separated, dried over Na₂SO₄ and filtered. The filtrate was evaporated to dryness. The residue was purified by column chromatography (silica gel, EtOAc/n-heptane=1/1 to 3/1, v/v) and further purified by recrystallization from EtOAc/n-heptane to give C5 as white needle crystals (16.7 g, 55%). ¹H NMR (400 MHz, CDCl₃) δ=7.43 (s, 1H), 4.10-3.78 (m, 2H), 3.55-3.38 (m, 2H), 2.10 (s, 3H), 1.94 (s, 3H), 1.76-1.58 (m, 4H), 1.45 (s, 9H).

Step d

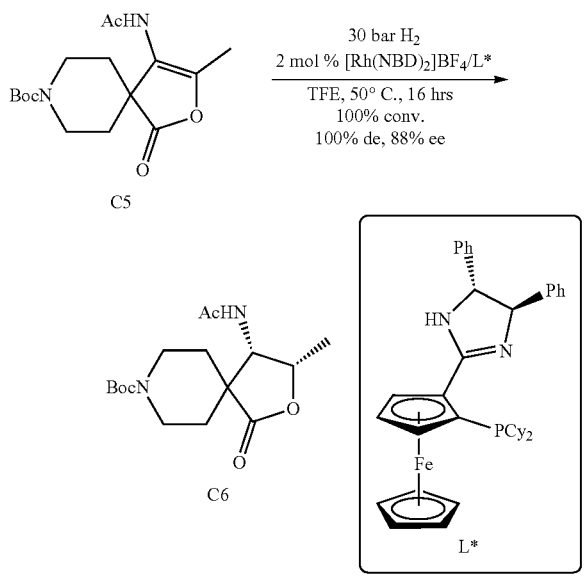

To a vial under a nitrogen atmosphere was added [Rh(NBD)₂]BF₄ (2.0 mg, 0.005 mmol), ligand L* (from Johnson Matthey & Brandenberger AG, Zurich, Schweiz) (3.3 mg, 0.005 mmol) and DCM (1 mL). The resulting solution was stirred for 30 minutes before solvent was removed to give a yellow solid. To the vial under a nitrogen atmosphere was added tert-butyl 4-acetamido-3-methyl-1-oxo-2-oxa-8-azaspiro[4.5]dec-3-ene-8-carboxylate C5 (86 mg, 0.27 mmol) and 2,2,2-trifluoroethanol (TFE) (2.7 mL). The vial was placed into a hydrogenation reactor. The reactor was purged with nitrogen three times and then with hydrogen three times. The mixture was stirred for 16 hrs under a hydrogen pressure of 30 bar at IT=50° C. The reaction was cooled to 20-25° C., filtered through a short silica pad and concentrated to dryness to give C6 as a white solid (86 mg, 100%). ¹H NMR (400 MHz, DMSO-d₆) δ=8.33 (br d, J=10.3 Hz, 1H), 4.94-4.84 (m, 1H), 4.71-4.56 (m, 1H), 3.78-3.65 (m, 2H), 3.22-3.02 (m, 1H), 2.87-2.69 (m, 1H), 1.89 (s, 3H), 1.64-1.50 (m, 4H), 1.40 (s, 9H), 1.19 (d, J=6.7 Hz, 3H).

Step e

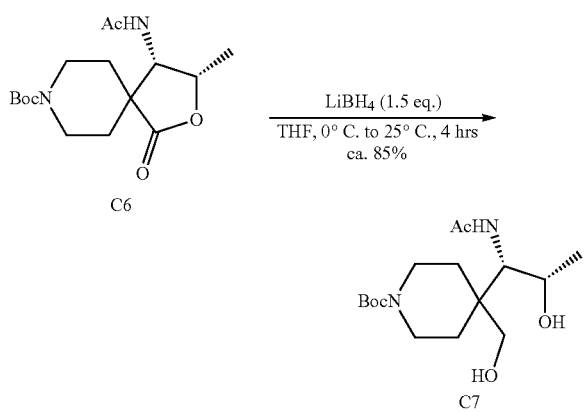

To a 10 mL Schlenk flask under a nitrogen atmosphere was added tert-butyl (3S,4S)-4-acetamido-3-methyl-1-oxo-2-oxa-8-azaspiro[4.5]decane-8-carboxylate C6 (300 mg, 0.919 mmol) and THF (3.0 mL). The flask was cooled in an ice-water bath. 2.0M LiBH₄ in THF (0.7 mL) was added dropwise and the reaction was stirred for 4 hrs at 20-25° C. The reaction was cooled in an ice-water bath and quenched by adding 5 wt % NaHCO₃ (1.0 mL) dropwise. The mixture was separated and the water layer was extracted by EtOAc (10 mL×3). The combined extracts were washed with 20 wt % brine (20 mL). The organic layer was separated, dried over Na₂SO₄ and filtered. The filtrate was evaporated to dryness. The residue was purified by column chromatography (silica gel, EtOAc/n-heptane=1/1 to 1/3, v/v) to give C7 as a colorless viscous oil (258 mg, 85%). ¹H NMR (400 MHz, DMSO-d₆) δ=7.48 (br d, J=10.1 Hz, 1H), 5.23 (br s, 1H), 5.15 (br s, 1H), 4.09-4.04 (m, 1H), 3.92-3.82 (m, 1H), 3.75 (d, J=10.1 Hz, 1H), 3.56 (d, J=5.1 Hz, 1H), 3.54-3.44 (m, 4H), 1.98 (s, 3H), 1.68-1.57 (m, 2H), 1.52-1.46 (m, 2H), 1.44 (s, 9H), 1.00 (d, J=6.2 Hz, 3H).

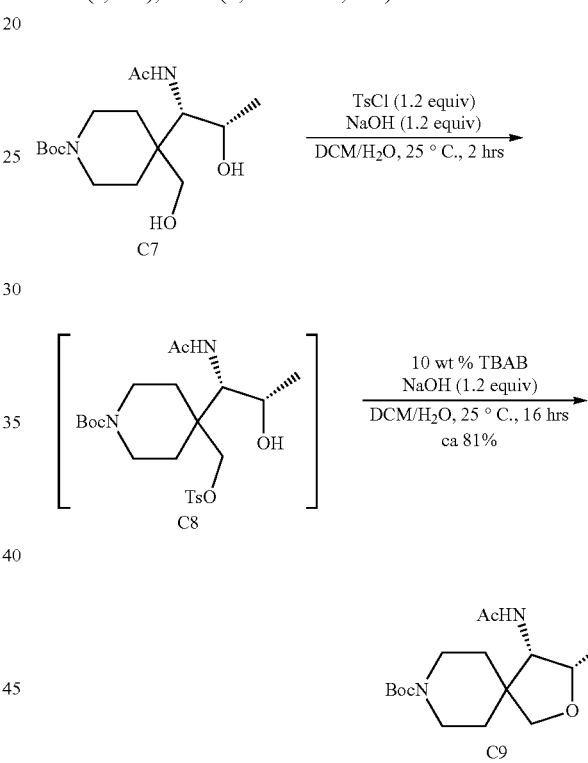

To a 25 mL Schlenk tube under a nitrogen atmosphere was added NaOH (94 mg, 2.35 mmol) and water (5.0 mL). The tube was cooled in an ice-water bath and a solution of tert-butyl 4-((1S,2S)-1-acetamido-2-hydroxypropyl)-4-(hydroxymethyl)piperidine-1-carboxylate C7 (650 mg, 1.97 mmol) and TsCl (450 mg, 2.36 mmol) in DCM (5.0 mL) was added dropwise. The mixture was then stirred for 16 hrs at 20-25° C. n-Bu₄NBr (65 mg, 0.202 mmol) was added followed by NaOH (94 mg, 2.35 mmol) in water (2.0 mL). The mixture was then stirred for 16 hrs at 20-25° C. The organic layer was separated, washed with 20 wt % brine (5 mL), dried over Na₂SO₄ and filtered. The filtrate was evaporated to dryness to give C9 as a white solid (500 mg, 81%). ¹H NMR (400 MHz, DMSO-d₆) δ=7.82 (br d, J=10.0 Hz, 1H), 4.18-4.06 (m, 2H), 3.65-3.56 (m, 1H), 3.55 (ABq, J=8.7 Hz, 2H), 3.32-3.11 (m, 3H), 1.89 (s, 3H), 1.57-1.40 (m, 4H), 1.38 (s, 9H), 1.01 (d, J=6.1 Hz, 3H).

Step f

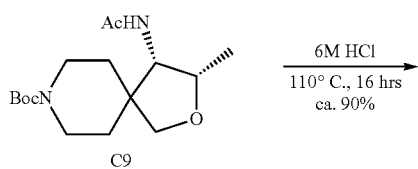

To a 10 mL sealed tube was added tert-butyl (3S,4S)-4-acetamido-3-methyl-2-oxa-8-azaspiro[4.5]decane-8-carboxylate C9 (25 mg, 0.077 mmol) and 6N aq. HCl (1.0 mL). The reaction was stirred for 16 hrs in a 110° C. oil bath. The reaction was then cooled to 20-25° C. and concentrated to dryness to give C10 as a white solid (17.0 mg, 90%). $^1$H NMR (400 MHz, DMSO-$d_6$) δ=9.37 (br s, 1H), 9.25 (br s, 1H), 8.42 (br s, 3H), 4.26-4.17 (m, 1H), 3.72 (ABq, J=9.1 Hz, 2H), 3.50-3.41 (m, 1H), 3.28-3.18 (m, 1H), 3.18-3.09 (m, 1H), 2.99-2.74 (m, 2H), 2.07-1.63 (m, 4H), 1.22 (d, J=6.5 Hz, 3H).

Step g

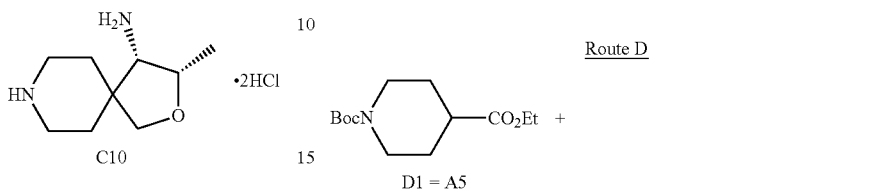

To a 10 mL Schlenk tube was added 3-((2-amino-3-chloropyridin-4-yl)thio)-6-chloropyrazin-2-amine Y10a (0.1 g, 0.347 mmol), (3S,4S)-3-methyl-2-oxa-8-azaspiro[4.5]decan-4-amine dihydrochloride C10 (0.1 g, 0.416 mmol, 1.2 eq), DMAc (0.6 mL) and 36 wt % aq. $K_2CO_3$ (0.66 g, 1.735 mmol, 5.0 eq). The mixture was stirred for 16 hrs in a 100° C. oil bath and cooled to 20-25° C. 20 wt % Brine (10 mL) was added and the mixture was extracted with EtOAc (20 mL×2). The combined extracts were washed with 20 wt % Brine (10 mL×4), dried over anhydrous $Na_2SO_4$ and filtered. The filtrate was concentrated to dryness to give C11 as a yellow solid (121 mg, 83%). $^1$H NMR (400 MHz, DMSO-$d_6$) δ=7.64 (d, J=6.2 Hz, 1H), 7.62 (s, 1H), 6.26 (s, 2H), 6.13 (s, 2H), 5.74 (d, J=5.3 Hz, 1H), 4.12-4.02 (m, 1H), 3.90-3.78 (m, 2H), 3.67 (d, J=8.4 Hz, 1H), 3.49 (d, J=8.4 Hz, 1H), 3.33 (s, 2H), 2.91 (d, J=5.1 Hz, 1H), 1.78-1.68 (m, 1H), 1.67-1.57 (m, 1H), 1.56-1.41 (m, 2H), 1.08 (d, J=6.5 Hz, 3H).

Example 3

Route D

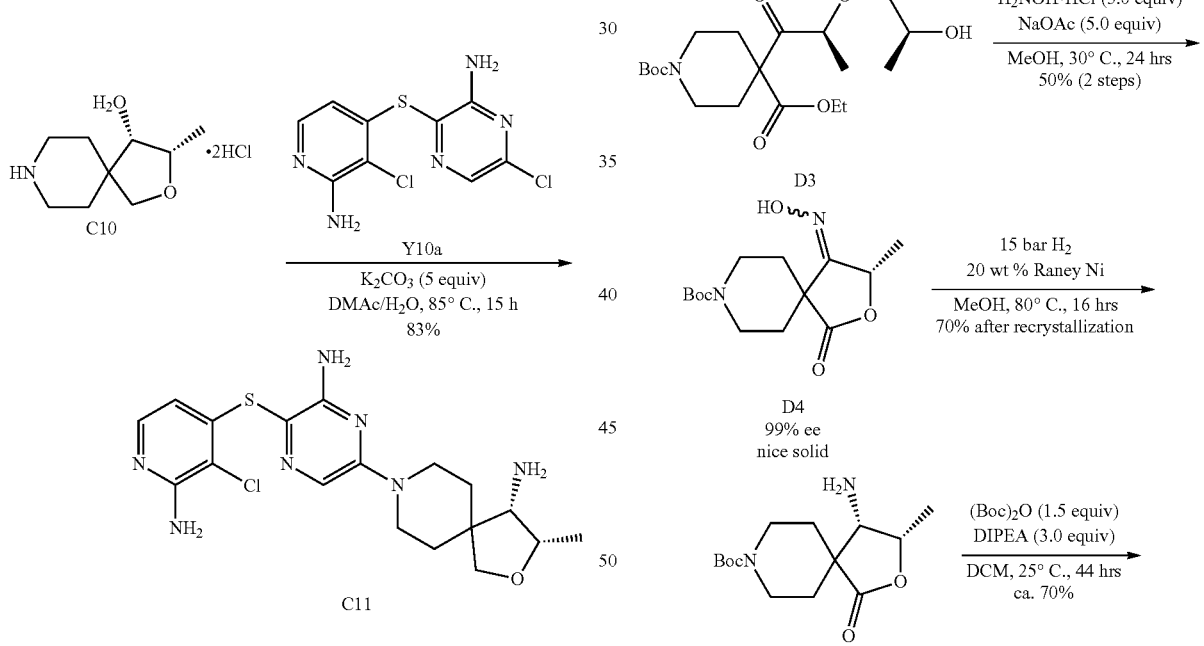

-continued

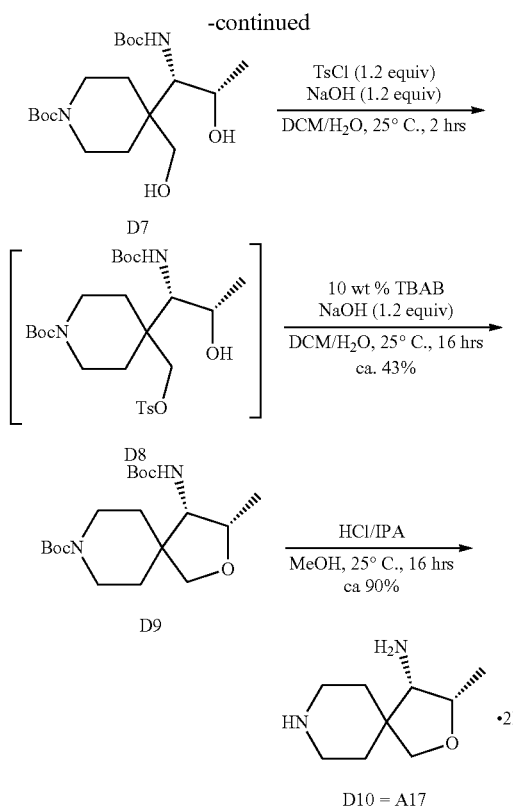

Step a:

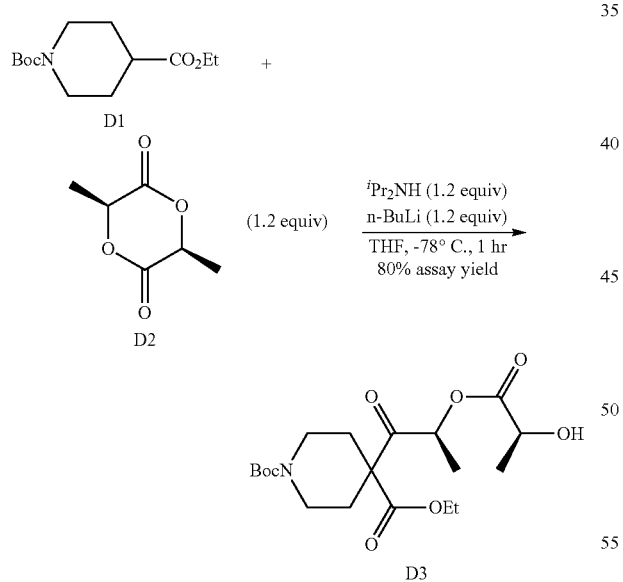

A 500 mL three-necked round bottomed flask A under an nitrogen atmosphere was charged with diisopropylamine (9.44 g, 93.3 mmol, 1.2 eq) and THF (200 mL). The solution was cooled to an IT=−20° C., 2.4 M n-BuLi in hexanes (38.9 mL, 1.2 eq) was added dropwise during 30 min. The reaction was stirred at −20° C. for 30 min and then cooled to −70° C. A solution of 1-(tert-butyl) 4-ethyl piperidine-1,4-dicarboxylate (D1) (20.0 g, 77.7 mmol, 1.0 eq) in THF (20 mL) was added dropwise during 30 min while maintaining the IT=−70° C. to −60° C. The reaction was stirred at −70° C. for 30 min and a pale yellow solution was obtained.

A 500 mL three-necked round bottomed flask B under an nitrogen atmosphere was charged with L-lactide (13.4 g, 93.3 mmol, 1.2 eq) and THF (120 mL). The solution was cooled to an IT=−70° C. The solution in flask A was transferred slowly to flask B via cannula during 30 min while maintaining the IT=−70° C. to −60° C. The reaction was stirred at −70° C. for 30 min. The reaction solution was transferred to flask C containing 3% HCl (300 mL) via cannula during 30 min while maintaining the IT=0° C. to 5° C. The mixture was extracted with EtOAc (400 mL×2) and washed with 20 wt % brine (200 mL). The organic layer was separated, dried over anhydrous Na$_2$SO$_4$ and filtered. The filtrate was concentrated to dryness to give D3 as a pale yellow oil (36.0 g, 71 wt %, 81% assay yield), which was used in the next step without further purification. $^1$H NMR (400 MHz, CDCl$_3$) δ=5.42 (q, J=6.8 Hz, 1H), 4.36-4.27 (m, 1H), 4.27-4.16 (m, 2H), 3.71-3.49 (m, 2H), 3.39-3.24 (m, 2H), 2.81 (br d, J=5.0 Hz, 1H), 2.24-1.81 (m, 4H), 1.44 (s, 15H), 1.27 (t, J=7.1 Hz, 3H).

Step b

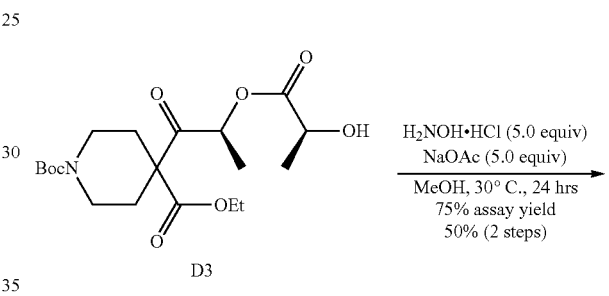

To a 250 mL round bottomed flask was added the above yellow oil (15.0 g, 71 wt %, 26.5 mmol), hydroxylamine hydrochloride (9.3 g, 132.6 mmol, 5.0 eq), sodium acetate (10.9 g, 132.6 mmol, 5.0 eq) and methanol (150 mL). The mixture was stirred for 24 hrs at 20-25° C. The resulting suspension was filtered through MCC and the filter cake was washed with MeOH (20 mL×2). The filtrate was concentrated to ca. 60 mL, water (60 mL) was then added dropwise during 15 min, a white solid precipitated out. The suspension was stirred overnight and filtered. The filter cake was washed with a mixture of MeOH (5 mL) and water (25 mL) and dried under vacuum to give D4 as a white solid (4.9 g, 59%). $^1$H NMR (400 MHz, DMSO-d$_6$) δ=11.45 (s, 1H), 5.33 (q, J=6.6 Hz, 1H), 3.73-3.58 (m, 2H), 3.56-3.43 (m, 1H), 3.43-3.35 (m, 1H), 1.87-1.65 (m, 4H), 1.52 (d, J=6.7 Hz, 3H), 1.41 (s, 9H).

Step c

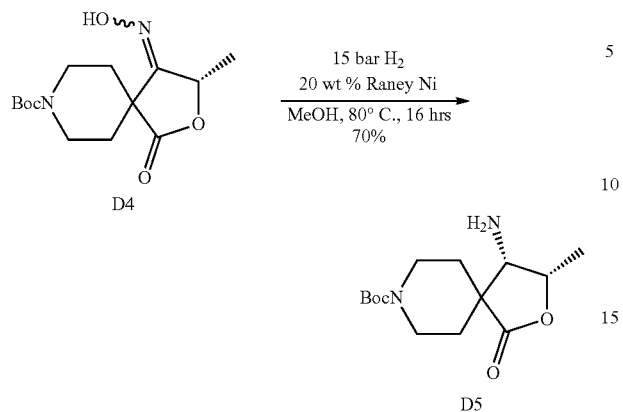

To a 1 L reactor with an impeller stirrer under an nitrogen atmosphere was added Raney-Ni (5 g) and MeOH (250 mL), followed by tert-butyl (S)-4-(hydroxyimino)-3-methyl-1-oxo-2-oxa-8-azaspiro[4.5]decane-8-carboxylate D4 (25.0 g, 83.80 mmol). The reactor was purged with nitrogen three times and then with hydrogen three times. The mixture was stirred for 16 hrs under a hydrogen pressure of 20 bar at IT=80° C. The reaction mixture was filtered through microcrystalline cellulose and the filter cake was washed with MeOH (10 ml). The filtrate was concentrated to dryness to give a white solid (23.0 g). EtOAc (220 mL) was added to the solid, the resulting suspension was heated to reflux (IT=100° C.) and n-heptane (550 mL) was added portionwise. The resulting clear solution was cooled to rt during 2 hrs and left standing overnight to give D5 as colorless crystals (16.7 g, cis/trans>99:1, 70%). $^1$H NMR (400 MHz, CDCl$_3$) δ=4.75-4.64 (m, 1H), 3.89-3.80 (m, 1H), 3.68-3.58 (m, 1H), 3.48-3.33 (m, 3H), 1.92-1.61 (m, 4H), 1.46 (s, 9H), 1.40 (d, J=6.5 Hz, 3H).

Step d

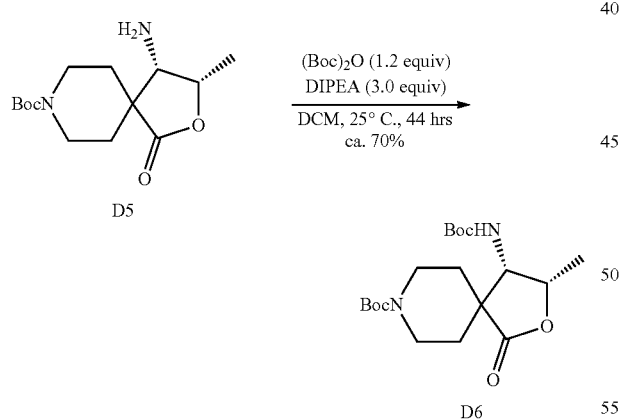

To a 10 mL Schlenk tube was added tert-butyl (3S,4S)-4-amino-3-methyl-1-oxo-2-oxa-8-azaspiro[4.5]decane-8-carboxylate D5 (100 mg, 0.352 mmol) and DCM (5.0 mL). The tube was cooled in an ice-water bath. Diisopropylamine (182 mg, 1.41 mmol) was added dropwise followed by Boc$_2$O (230 mg, 1.05 mmol). The reaction was then stirred for 44 hrs at 20-25° C. The organic layer was separated, washed with 20 wt % brine (5 mL), dried over Na$_2$SO$_4$ and filtered. The filtrate was evaporated to dryness to give D6 as a colorless oil (95 mg, 70%), which gradually solidified upon standing. HRMS m/z calcd for C$_{19}$H$_{33}$N$_2$O$_6$ [M+H]$^+$ 385.2333, found 385.2334.

Step e

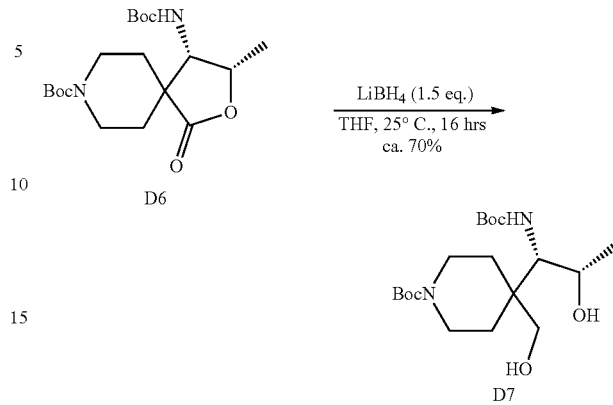

To a 10 mL Schlenk flask under a nitrogen atmosphere was added tert-butyl (3S,4S)-4-((tert-butoxycarbonyl)amino)-3-methyl-1-oxo-2-oxa-8-azaspiro[4.5]decane-8-carboxylate D6 (126 mg, 0.335 mmol) and THF (3.0 mL). The flask was cooled in an ice-water bath. 2.0M LiBH$_4$ in THF (0.25 mL) was added dropwise and the reaction was stirred for 16 hrs at 20-25° C. The reaction was cooled in an ice-water bath and quenched by adding 5 wt % NaHCO$_3$ (1.0 mL) dropwise. The mixture was separated and the water layer was extracted by EtOAc (10 mL×3). The combined extracts were washed with 20 wt % brine (20 mL). The organic layer was separated, dried over Na$_2$SO$_4$ and filtered. The filtrate was evaporated to dryness to give D7 as a colorless viscous oil (91 mg, 70%). HRMS m/z calcd for C$_{19}$H$_{37}$N$_2$O$_6$ [M+H]$^+$ 389.2646, found 389.2628.

Step f

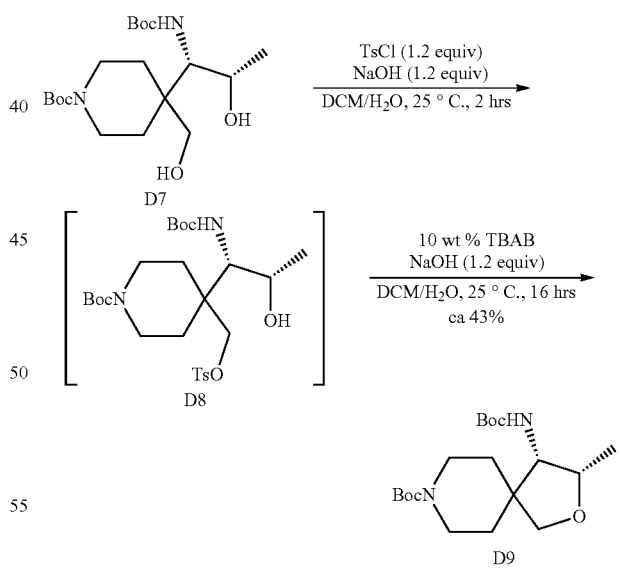

To a 25 mL Schlenk tube under a nitrogen atmosphere was added NaOH (14 mg, 0.34 mmol) and water (2.0 mL). The tube was cooled in an ice-water bath and a solution of tert-butyl 4-((1S,2S)-1-((tert-butoxycarbonyl)amino)-2-hydroxypropyl)-4-(hydroxymethyl)piperidine-1-carboxylate D7 (110 mg, 0.283 mmol) and TsCl (65 mg, 0.34 mmol) in DCM (2.0 mL) was added dropwise. The mixture was then stirred for 16 hrs at 20-25° C. n-Bu$_4$NBr (9.1 mg, 0.028 mmol) was added followed by NaOH (14 mg, 0.34 mmol) in water (1.0 mL). The mixture was then stirred for 16 hrs at 20-25° C. The organic layer was separated, washed with 20 wt % brine (2 mL), dried over Na$_2$SO$_4$ and filtered. The filtrate was evaporated to dryness to give D9 as a colorless oil (45 mg, 43%). HRMS m/z calcd for C$_{19}$H$_{35}$N$_2$O$_5$ [M+H]$^+$ 371.2540, found 371.2533.

Step g

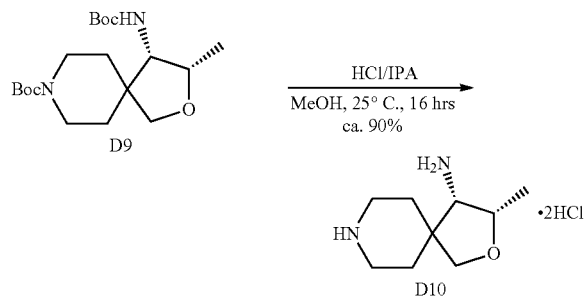

To a 10 mL Schlenk tube was added tert-butyl (3S,4S)-4-((tert-butoxycarbonyl)amino)-3-methyl-2-oxa-8-azaspiro[4.5]decane-8-carboxylate D9 (100 mg, 0.27 mmol), 6N HCl in isopropanol (1.0 mL) and methanol (3.0 mL). The reaction was stirred for 16 hrs at 20-25° C. and concentrated to dryness to give D10 as a white solid (59 mg, 90%). $^1$H NMR (400 MHz, DMSO-d$_6$) δ=9.37 (br s, 1H), 9.25 (br s, 1H), 8.42 (br s, 3H), 4.26-4.17 (m, 1H), 3.72 (ABq, J=9.1 Hz, 2H), 3.50-3.41 (m, 1H), 3.28-3.18 (m, 1H), 3.18-3.09 (m, 1H), 2.99-2.74 (m, 2H), 2.07-1.63 (m, 4H), 1.22 (d, J=6.5 Hz, 3H).

Step h

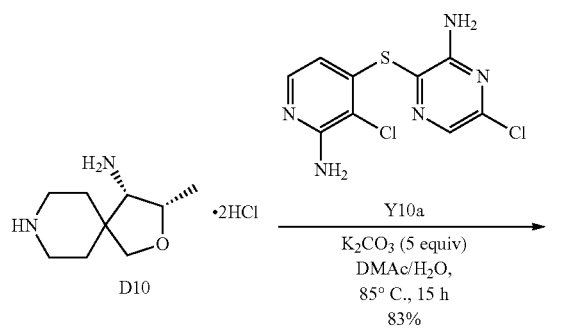

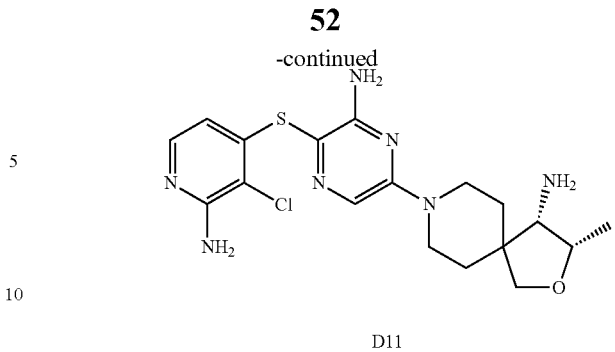

To a 10 mL Schlenk tube was added 3-((2-amino-3-chloropyridin-4-yl)thio)-6-chloropyrazin-2-amine Y10a (0.1 g, 0.347 mmol), (3S,4S)-3-methyl-2-oxa-8-azaspiro[4.5]decan-4-amine dihydrochloride D10 (0.1 g, 0.416 mmol, 1.2 eq), DMAc (0.6 mL) and 36 wt % aq. K$_2$CO$_3$ (0.66 g, 1.735 mmol, 5.0 eq). The mixture was stirred for 16 hrs in a 100° C. oil bath and cooled to 20-25° C. 20 wt % Brine (10 mL) was added and the mixture was extracted with EtOAc (20 mL×2). The combined extracts were washed with 20 wt % Brine (10 mL×4), dried over anhydrous Na$_2$SO$_4$ and filtered. The filtrate was concentrated to dryness to give D11 as a yellow solid (121 mg, 83%). $^1$H NMR (400 MHz, DMSO-d$_6$) δ=7.64 (d, J=6.2 Hz, 1H), 7.62 (s, 1H), 6.26 (s, 2H), 6.13 (s, 2H), 5.74 (d, J=5.3 Hz, 1H), 4.12-4.02 (m, 1H), 3.90-3.78 (m, 2H), 3.67 (d, J=8.4 Hz, 1H), 3.49 (d, J=8.4 Hz, 1H), 3.33 (s, 2H), 2.91 (d, J=5.1 Hz, 1H), 1.78-1.68 (m, 1H), 1.67-1.57 (m, 1H), 1.56-1.41 (m, 2H), 1.08 (d, J=6.5 Hz, 3H).

Example 4

(3-((2-amino-3-chloropyridin-4-yl)thio)-6-chloropyrazin-2-amine)

Compound Y7a=Y10a mentioned above (3-((2-amino-3-chloropyridin-4-yl)thio)-6-chloropyrazin-2-amine) was obtained as follows:

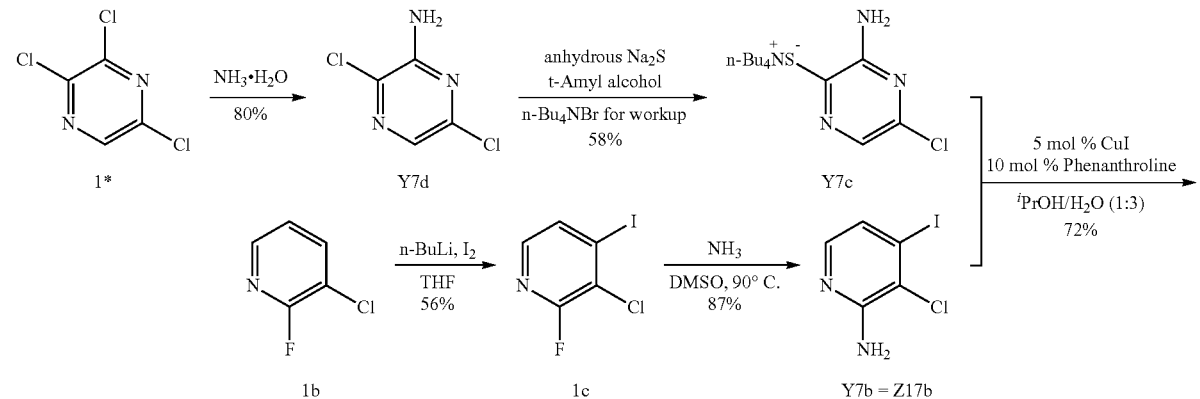

Step a

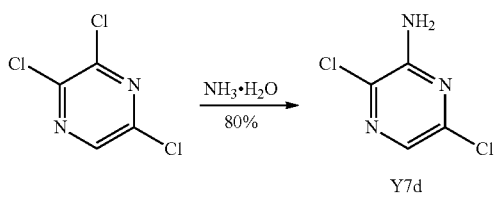 [SMILES: Clc1cnc(Cl)c(Cl)n1 ; "NH3·H2O" ; Nc1nc(Cl)cnc1Cl]

2,3,5-trichloropyrazine (70.50 g, 384.36 mmol, 1 equiv) and ammonia solution (25% wt, 364.00 g, 400 mL, 2.68 mol, 6.14 equiv) were added to a 1-L sealed reactor. The mixture was heated to 80° C. and stirred for 24 h, and the reaction was completed. The reaction mixture was cooled to 30° C. and filtered to give a brown filter cake. The brown filter cake was dissolved in acetone (50 mL), and filtered. To the filtrate was added petroleum ether (300 mL). The suspension was stirred for 4 h, and filtered to give the crude product. The crude product was slurried in combined solvents of petroleum ether and acetone (10/1, 200 mL) and filtered to give the product Y7d (51.00 g, 307.91 mmol, 80% yield) as a light yellow solid. 1H NMR (400 MHz, DMSO-$d_6$) δ=7.63 (s, 1H). The advantage of this (also generalized) method is that no column chromatography is required to obtain Y7d.

Step b

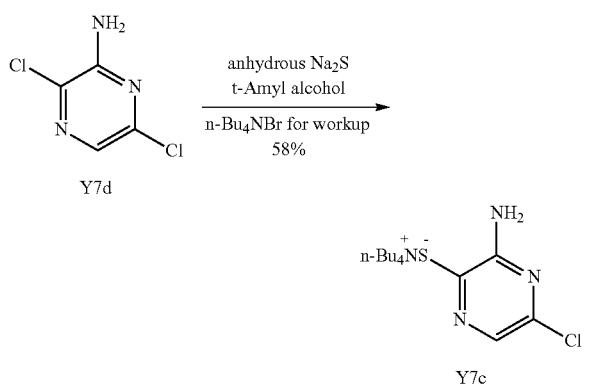

To a 200 mL round bottom flask was added Na$_2$S (10.816 g, 44 wt % containing crystalline water, 60.978 mmol) and toluene (100 mL). The mixture was heated to reflux, and water was removed with a Dean-Stark trap (about 5-6 mL water was distilled out). After cooling, the mixture was concentrated to dry.

To above round bottom flask was added Y7d (5.000 g, 30.489 mmol) and 2-methylbutan-2-ol (50 mL), the reaction was heated to reflux and stirred for 36 h. After cooling to 25° C., the mixture was filtered. The solvent of the filtrate was exchanged with n-heptane (5 V*3 times, based on Y7d), and

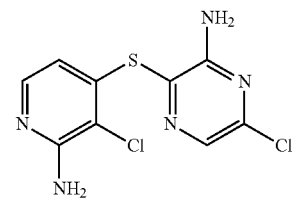

finally concentrated to 1V residue. THF (25 mL) was charged to the residue at 25° C. and stirred. The suspension was filtered and washed with THF/n-heptane (5 mL/5 mL) to give a brown solid (6.200 g).

To another 200 mL round bottom flask was added above brown solid (6.200 g), 10% brine (25 mL), Me-THF (30 mL) and n-Bu$_4$NBr (9.829 g, 30.489 mmol). The mixture was stirred for 0.5 h at room temperature, and the phases were separated. The organic phase was washed with 20% brine (25 mL), and exchanged the solvent with iso-propanol (5 V*3 times, based on Y7d) to give the iso-propanol solution of Y7c (27.000 g, 99.2% purity by HPLC area, 58.08% assay yield). 1H NMR (400 MHz, DMSO-$d_6$) δ=6.88 (s, 1H), 2.97-2.92 (m, 14H), 1.38-1.31 (m, 14H), 1.13-1.04 (m, 14H), 0.73-0.69 (t, 21H). The advantage of the use of n-Bu$_4$NBr (or other corresponding tert-alkylaminohalogenide) is easier workup and purification.

Step c

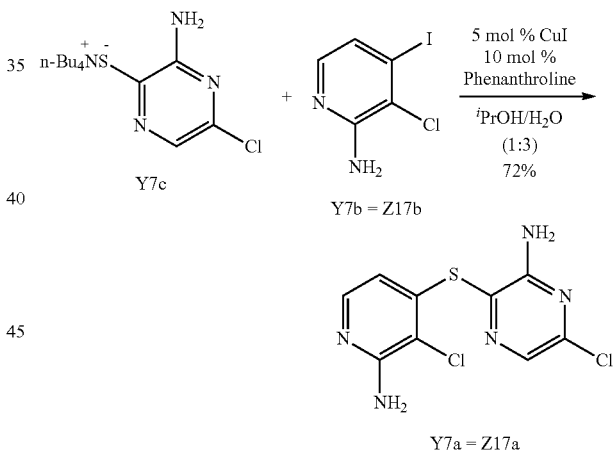

To a 25-mL round-bottom flask was added Y7c (4.7 g, 23.27 wt %, IPA solution, 2.723 mmol, 1.0 equiv), Y7b (1.052 g, 4.085 mmol, 1.5 equiv), 1,10-Phenanthroline (0.05 g, 0.272 mmol) and water (8 mL). The mixture was purged with nitrogen gas three times, and CuI (0.026 g, 0.136 mmol) was added under nitrogen atmosphere. The mixture was heated up to 65° C. and stirred for 3 h, and the reaction was completed. The reaction was cooled to room temperature and filtered, and the filter cake was washed with water (4 mL*3). The filter cake was slurried in MTBE (6 mL) for 30 min and filtered. The filter cake was washed with MTBE (6 mL) and dried to afford Y7a=Z17a which is the compound of the formula Y10a mentioned in step g) of Example 2 and of step h) of Example 3 (565 mg, 72% yield). The reaction can be led using copper instead of palladium catalysis for the coupling of Y7b with Y7c.

Example 5

(3-((2-amino-3-chloropyridin-4-yl)thio)-6-chloropyrazin-2-amine)

The compound of formula Z17a=Y10a is alternatively made according to the following reaction scheme:

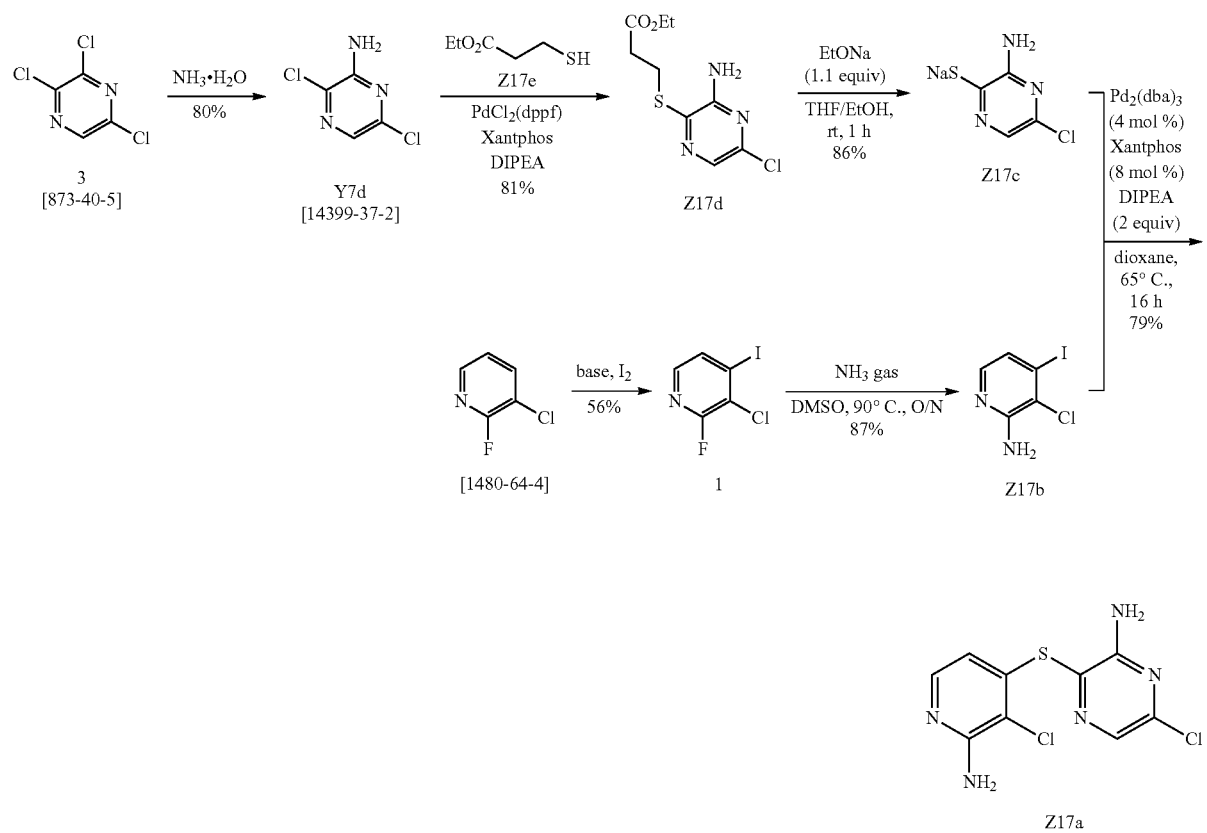

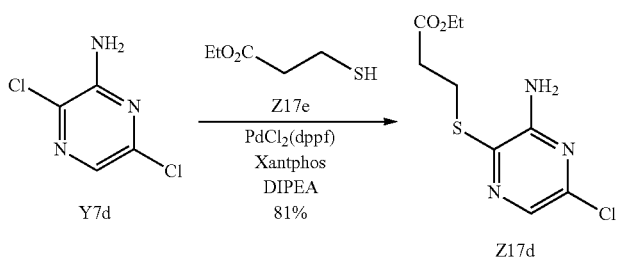

To a three-necked round-bottle flask was added Y7d (200 mg, 1.22 mmol, 1 equiv), dioxane (4 mL). The solution was vacuated and purged with nitrogen gas three times. Xantphos (14 mg, 0.024 mmol, 0.02 equiv), PdCl$_2$(dppf) (8.9 mg, 0.012 mmol, 0.1 equiv), and DIPEA (0.32 g, 2.44 mmol, 2.0 equiv) were added under nitrogen atmosphere. The solution was heated to 85° C. for overnight. The reaction was cooled and evaporated. The residue was purified by column chromatography (eluent/ethyl acetate/heptane=1/1) to give Z17d (259 mg, 0.99 mmol, 81%). $^1$H NMR (400 MHz, CDCl$_3$) δ=7.83 (s, 1H), 4.88 (bs, 2H), 3.73 (s, 3H), 3.47 (t, J=9.2 Hz, 2H), 2.79 (t, J=9.2 Hz, 2H).

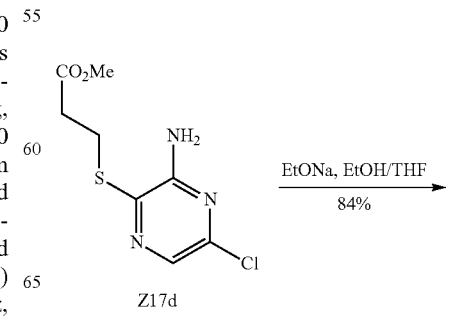

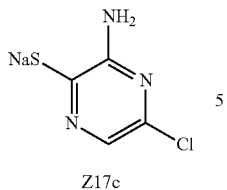

To a solution of Z17d (8.0 kg, assay 95%, 30.68 mol) in THF (70 L) was added EtONa (prepared from 776 g Na and 13.6 L EtOH) at room temperature and the mixture was stirred at ambient temperature for 1 hour. The mixture was then concentrated to a wet yellow solid by rotary evaporation and the residue was suspended in DCM (40 L). The mixture stirred under $N_2$ for 16 h. The solids were collected by vacuum filtration and the cake was washed with DCM (about 15 L) until the filtrate was colorless (PSC-2). The solids were then dried under vacuum to give Z17c (6.93 kg, qNMR 72%, yield 88%). $^1$H NMR (400 MHz, D2O) δ=7.37 (s, 1H).

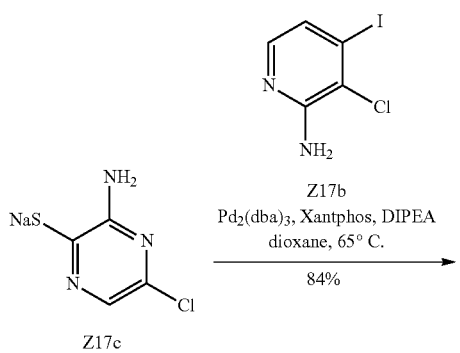

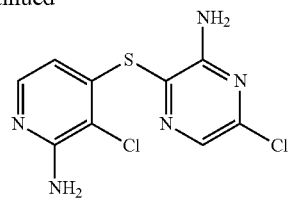

To a mixture of Z17c (6.95 kg, assay 72%, 27.23 mol) in 1,4-dioxane (72 L) was added Xantphos (233 g, 411 mmol, 0.015 eq), $Pd_2(dba)_3$ (186 g, 206 mmol, 0.0075 eq), Z17b (7.13 kg, 28.02 mol) and DIPEA (7.02 kg, 54.46 mol). The system was vacuated and purged with nitrogen gas three times. The mixture was stirred at 65° C. for 16 h under $N_2$. The mixture was cooled to rt and water (50 L) was added, filtered. The cake was washed with EA (25 L). The filtrate was extracted with EA (4×20 L). The organic phase was concentrated in vacuum to offer the crude product which was combined with the cake. Then DCM (60 L) was added to the crude product and stirred at 25-30° C. for 18 h and then filtered. The filter cake was slurried with $CH_2Cl_2$ (30 L) for 4 hrs and filtered. The filter cake was slurred in $CH_2Cl_2$ (30 L) for 16 hrs and filtered. Then the filter cake was dried in vacuum to give Z17a (9.1 kg, 84%) as light yellow solid. $^1$H NMR (400 MHz, DMSO-$d_6$) δ=7.89 (s, 1H), 7.7 (d, J=7.6 Hz, 1H), 7.18 (bs, 2H), 6.40 (bs, 2H), 5.97 (d, J=7.6 Hz, 1H)

Example 6

(3-((2-amino-3-chloropyridin-4-yl)thio)-6-chloropyrazin-2-amine)

The compound of formula Z17a=Y10a is alternatively made according to the following reaction scheme:

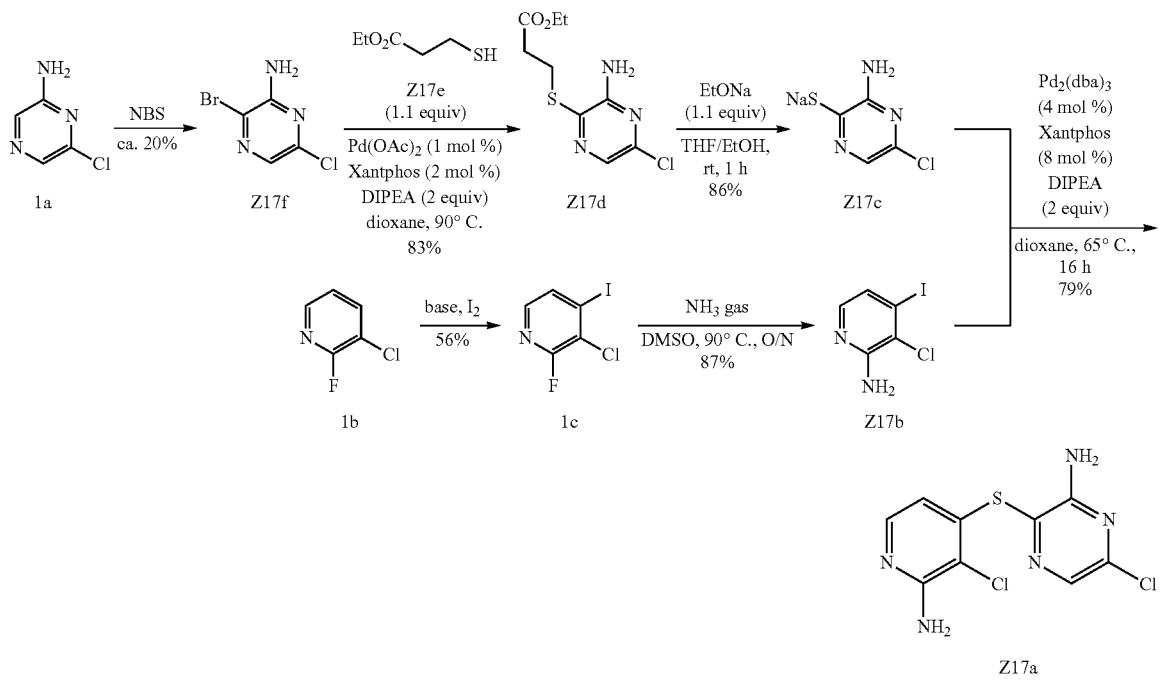

In detail, the synthesis of Compound Z17a was carried out as follows:

Step a

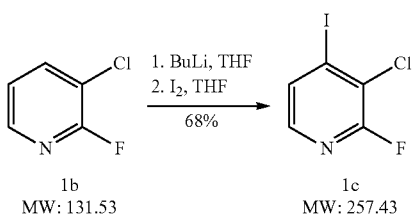 [SMILES: Fc1ncccc1Cl ; Fc1nccc(I)c1Cl]

1b
MW: 131.53

1c
MW: 257.43

Under nitrogen atmosphere, n-BuLi (2.5M, 7.6 L) was added dropwise to a solution of 3-chloro-2-fluoropyridine (2 kg) in THF (15 L) at −78° C. Then the resultant mixture was stirred for 1 h. Then a solution of $I_2$ (4.82 kg) in THF (6 L) was added dropwise. After addition, the reaction mixture was stirred for 30 min, and then quenched with sat. $Na_2SO_3$ (10 L), and warmed to 20-25° C. Phase was separated. The aqueous phase was extracted with EA (2×10 L). The combined organic phase was washed with sat. $Na_2SO_3$ (2×8 L), brine (8 L), and dried over $Na_2SO_4$. The organic phase was concentrated under vacuum. The residue was slurried in MeOH (4 L), filtered, and dried to offer 3-chloro-2-fluoro-4-iodopyridine 1c (2.2 kg, yield 68%).

Step b

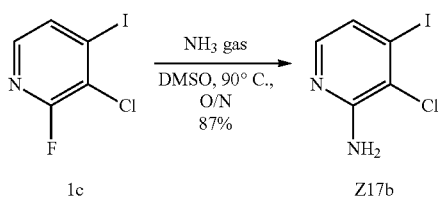 [SMILES: Fc1nccc(I)c1Cl ; Nc1nccc(I)c1Cl]

1c

Z17b

Into a solution of Compound 1c (8 kg) in DMSO (48 L) was passed through $NH_3$ (gas) at 80° C. overnight. TLC showed the reaction was finished. The reaction mixture was cooled to RT. The reaction mixture was added to water (140 L). The solid was collected and washed with water (25 L), dried to afford Z17b (6.91 kg, yield 87%). $^1$H NMR (400 MHz, CDCl3) δ=7.61 (d, J=6.8 Hz, 1H), 7.14 (s, J=6.8 Hz, 1H), 5.09 (bs, 2H).

Step c

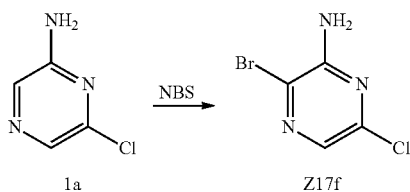

1a

Z17f

A solution of 2-amino-6-chloro-pyrazine 1a (1 kg, 7.69 mol) in DCM (15 L) was heated to reflux, to which was charged NBS (417 g) in portions during 1 h. The reaction was cooled to room temperature. The reaction mixture was washed with water (3 L) and brine (3 L). The organic phase was evaporated, and the residue was purified by column chromatography to give product Z17f (3-bromo-6-chloro-pyrazin-2-amine) (180 g, 11% yield).

Step d

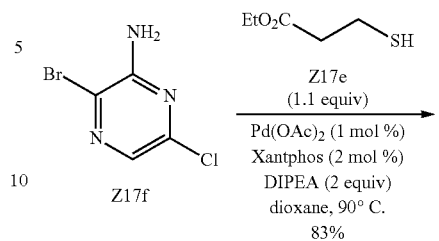

Z17f    Z17e

To a solution of 3-bromo-6-chloropyrazin-2-amine Z17f (6.0 kg, 28.78 mol) in 1,4-Dioxane (40 L) was added $Pd(OAc)_2$ (64.56 g, 287.6 mmol), Xantphos (333 g, 575.6 mmol), and DIPEA (7.44 kg, 57.56 mol) at room temperature under nitrogen. After another 30 minutes purging with nitrogen, methyl 3-mercaptopropanoate (3.81 kg, 31.70 mol) was added, resulting in darkening of the orange mixture. The mixture was heated to 90° C. HPLC showed complete conversion of the starting material. The mixture was allowed to cool to about room temperature, then diluted with EtOAc (40 L). After aging for 30 min with stirring, the entire mixture was filtered and solids were washed with EtOAc (3×15 L). The combined orange filtrate was concentrated to dryness and the solid residue was suspended in DCM (45 L). The mixture was heated to 35-40° C. and stirred for 1 h until all solids were dissolved. Then n-heptane (45 L) was added dropwise. Upon complete addition, the mixture was cooled to 15-20° C. with stirring for 1 h. The solids were collected by vacuum filtration and solids were washed with cold 1:1 DCM/heptane (25 L), then heptane (25 L) (PSC-2). The solids were dried over the weekend to give Z17d (5.32 kg, yield 75%). $^1$H NMR (400 MHz, CDCl3) δ=7.83 (s, 1H), 4.88 (bs, 2H), 3.73 (s, 3H), 3.47 (t, J=9.2 Hz, 2H), 2.79 (t, J=9.2 Hz, 2H).

Step e

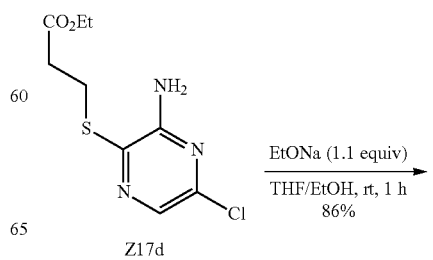

Z17d

-continued

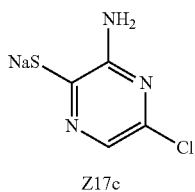

Z17c

To a solution of Z17d (8.0 kg, assay 95%, 30.68 mol) in THF (70 L) was added EtONa (prepared from 776 g Na and 13.6 L EtOH) at room temperature and the mixture was stirred at ambient temperature for 1 hour. The mixture was then concentrated to a wet yellow solid by rotary evaporation and the residue was suspended in DCM (40 L). The mixture stirred under $N_2$ for 16 h. The solids were collected by vacuum filtration and the cake was washed with DCM (about 15 L) until the filtrate was colorless (PSC-2). The solids were then dried under vacuum to give Z17c (6.93 kg, qNMR 72%, yield 88%). $^1$H NMR (400 MHz, D2O) δ=7.37 (s, 1H).

Step f

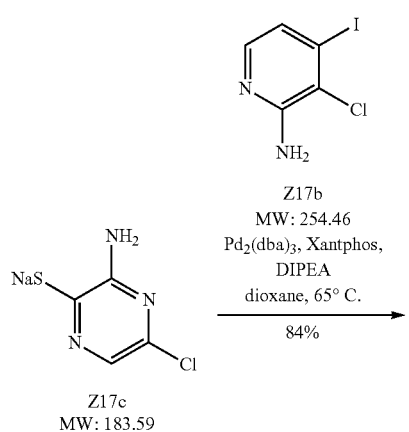

Z17b
MW: 254.46
$Pd_2(dba)_3$, Xantphos, DIPEA
dioxane, 65° C.
84%

Z17c
MW: 183.59

Z17a
MW: 288.16

To a mixture of Z17c (6.95 kg, assay 72%, 27.23 mol) in 1,4-dioxane (72 L) was added Xantphos (233 g, 411 mmol, 0.015 eq), $Pd_2(dba)_3$ (186 g, 206 mmol, 0.0075 eq), Z17b (7.13 kg, 28.02 mol) and DIPEA (7.02 kg, 54.46 mol). The system was vacuated and purged with nitrogen gas three times. The mixture was stirred at 65° C. for 16 h under $N_2$. The mixture was cooled to RT and water (50 L) was added, filtered. The cake was washed with EA (25 L). The filtrate was extracted with EA (4×20 L). The organic phase was concentrated in vacuum to offer the crude product which was combined with the cake. Then DCM (60 L) was added to the crude product and stirred at 25-30° C. for 18 h and then filtered. The filter cake was slurried with $CH_2Cl_2$ (30 L) for 4 hrs and filtered. The filter cake was slurred in $CH_2Cl_2$ (30 L) for 16 hrs and filtered. Then the filter cake was dried in vacuum to give Z17a (3-((2-amino-3-chloropyridin-4-yl)thio)-6-chloropyrazin-2-amine; 9.1 kg, 84%) as light yellow solid. $^1$H NMR (400 MHz, DMSO-d6) δ=7.89 (s, 1H), 7.7 (d, J=7.6 Hz, 1H), 7.18 (bs, 2H), 6.40 (bs, 2H), 5.97 (d, J=7.6 Hz, 1H).

The invention claimed is:

1. A method for the manufacture of a compound of Formula I, or a pharmaceutically acceptable salt, acid co-crystal, hydrate or other solvate thereof, said method comprising reacting a compound of formula II with a compound of formula III according to the following reaction scheme:

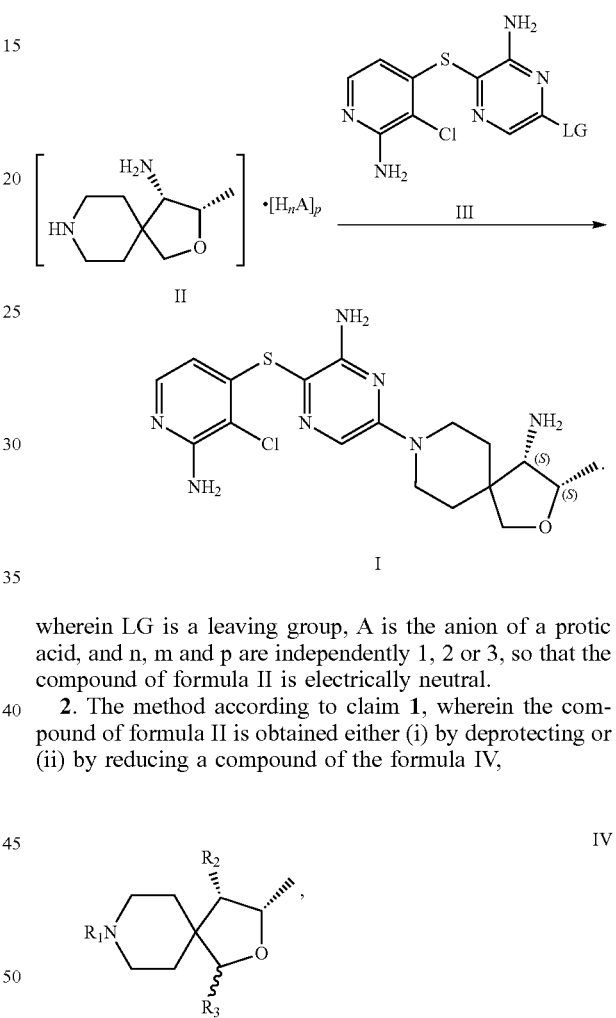

wherein LG is a leaving group, A is the anion of a protic acid, and n, m and p are independently 1, 2 or 3, so that the compound of formula II is electrically neutral.

2. The method according to claim 1, wherein the compound of formula II is obtained either (i) by deprotecting or (ii) by reducing a compound of the formula IV,

IV

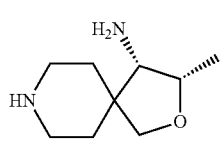

wherein in case (i) $R_1$ is a secondary amino protecting group and $R_2$ is a protected amino group and $R_3$ is hydrogen, or in case (ii) $R_1$ is a secondary amino protecting group, $R_2$ is amino and $R_3$ is hydroxyl, and if required, reacting the resulting compound of formula IVa:

IVa with an acid of the formula H$_n$A to yield the compound of formula II.

3. The method according to claim 2, wherein the compound of formula IV is a compound of formula IX:

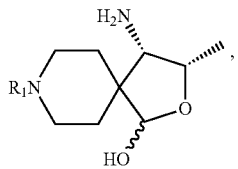

wherein R$_1$ is a secondary amino protecting group;
wherein the compound of formula IX is obtained by reducing a compound of formula VIII:

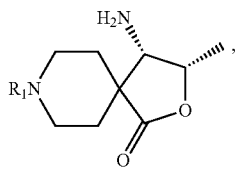

wherein R$_1$ is a secondary amino protecting group, to yield the compound of formula IX.

4. The method of claim 3, wherein the compound of formula VIII is obtained by hydrogenating a compound of formula VII:

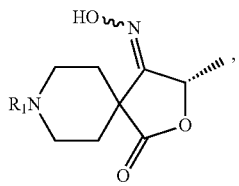

wherein R$_1$ is a secondary amino protecting group, to yield the compound of formula VIII.

5. The method of claim 4, wherein the compound of formula VII is obtained by cyclizing a compound of formula VI:

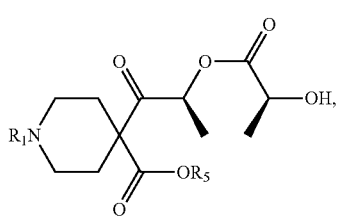

wherein R$_1$ a secondary amino protecting group and R$_5$ is unsubstituted or substituted alkyl, unsubstituted or substituted cycloalkyl or unsubstituted or substituted aryl, with hydroxylamine, or a salt thereof, to yield the compound of formula VII;

or alternatively by reacting a compound of formula VI*:

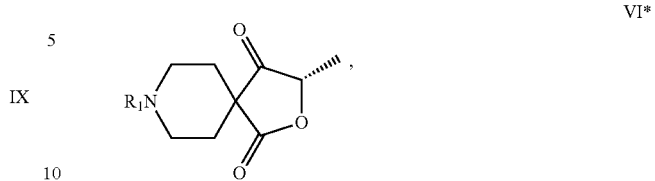

wherein R$_1$ is a secondary amino protecting group, with hydroxylamine, or a salt thereof, to yield the compound of formula VII.

6. The method of claim 5, wherein the compound of formula VI or the compound of formula VI* is obtained by reacting a compound of formula V:

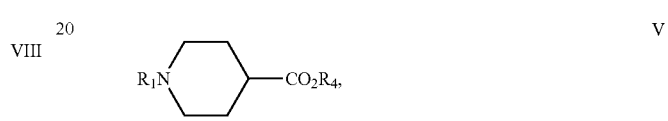

wherein R$_1$ is a secondary amino protecting group and R$_4$ is a carboxyl (—COOH) protecting group, in the presence of a strong base with L-lactide of the formula:

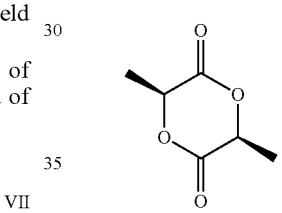

to yield the compound of formula VI or alternatively the compound of formula VI*.

7. The method of claim 4, wherein the compound of formula VII is obtained by reacting a compound of formula V:

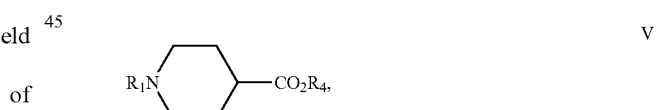

wherein R$_1$ is a secondary amino protecting group and R$_4$ is a carboxyl (—COOH) protecting group, in the presence of a strong base with L-lactide of the formula:

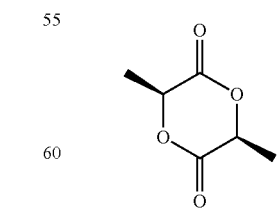

to provide an intermediate; and
subsequently reacting the intermediate with hydroxylamine, or a salt thereof, to yield the compound of formula VII.

8. The method of claim 2, wherein the compound of formula IV is a compound of formula XIII*:

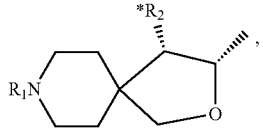

XIII* wherein $R_1$ is a secondary amino protecting group and $*R_2$ is an acylated amino group;

wherein the compound of formula XIII* is obtained by hydrogenating a compound of formula VIII*:

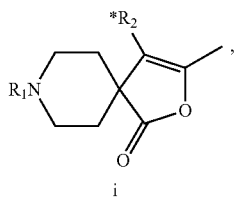

VIII* wherein $R_1$ is a secondary amino protecting group and $*R_2$ is an acylated amino group; in the presence of a chiral hydrogenation catalyst to yield a compound of formula X*:

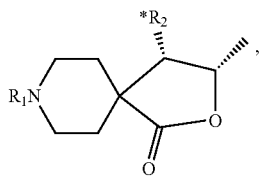

X* wherein $R_1$ is a secondary amino protecting group and $*R_2$ is an acylated amino group;

reducing the compound of formula X* to yield a compound of formula XI*:

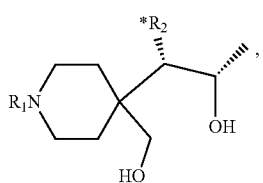

XI* wherein $R_1$ is a secondary amino protecting group and $*R_2$ is an acylated amino group;

reacting the compound of formula XI* with a leaving group forming agent of the formula LG*-X wherein LG* is an electrophilic radical capable of forming, with a hydroxy to which it is bound, a leaving group LG2, and X is halogen, to yield a compound of formula XII*:

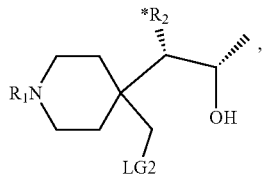

XII* wherein $R_1$ is a secondary amino protecting group, $*R_2$ is an acylated amino group, and LG2 is a leaving group; and cyclizing the compound of formula XII* under basic conditions to yield the compound of formula XIII*.

9. The method of claim 8, wherein the compound of formula VIII* is obtained by acylating a compound of formula VII:

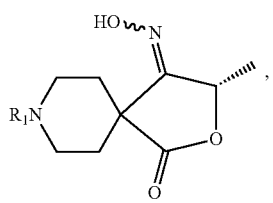

VII wherein $R_1$ a secondary amino protecting group, under reducing conditions to yield the compound of formula VIII*.

10. The method of claim 9, wherein the compound of formula VII is obtained by cyclizing a compound of formula VI:

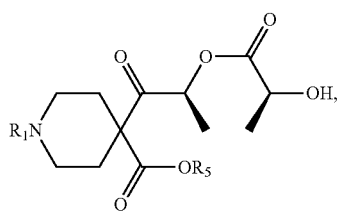

VI wherein $R_1$ a secondary amino protecting group and $R_5$ is unsubstituted or substituted alkyl, unsubstituted or substituted cycloalkyl or unsubstituted or substituted aryl, with hydroxylamine, or a salt thereof, to yield the compound of formula VII;

or alternatively by reacting a compound of formula VI*:

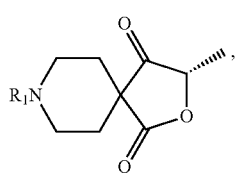

VI* wherein $R_1$ is a secondary amino protecting group, with hydroxylamine, or a salt thereof, to yield the compound of formula VII.

11. The method of claim 10, wherein the compound of formula VI or the compound of formula VI* is obtained by reacting a compound of formula V:

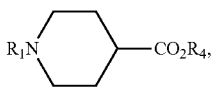

wherein R₁ is a secondary amino protecting group and R₄ is a carboxyl (—COOH) protecting group, in the presence of a strong base with L-lactide of the formula:

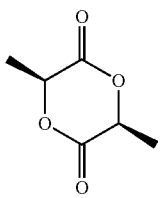

to yield the compound of formula VI or alternatively the compound of formula VI*.

12. The method of claim 9, wherein the compound of formula VII is obtained by reacting a compound of formula V:

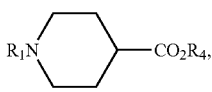

wherein R₁ is a secondary amino protecting group and R₄ is a carboxyl (—COOH) protecting group, in the presence of a strong base with L-lactide of the formula:

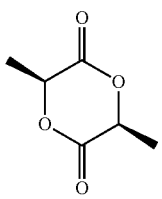

to provide an intermediate; and
subsequently reacting the intermediate with hydroxylamine, or a salt thereof, to yield the compound of formula VII.

13. The method of claim 2, wherein the compound of formula IV is a compound of formula XIII:

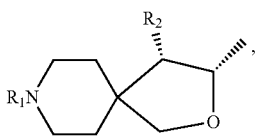

wherein R₁ is a secondary amino protecting group and R₂ is a protected amino group;
wherein the compound of formula XIII is obtained by reducing a compound of formula X:

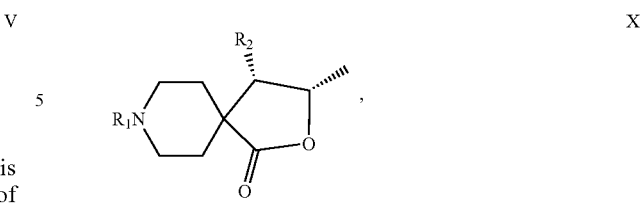

wherein R₁ is a secondary amino protecting group and R₂ is a protected amino group, to yield a compound of formula XI:

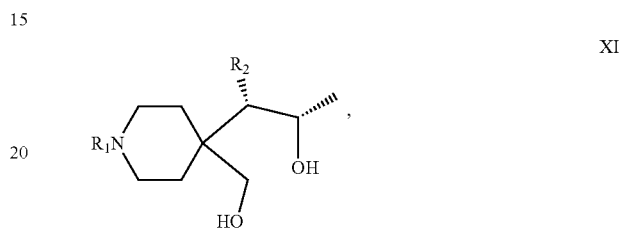

wherein R₁ is a secondary amino protecting group and R₂ is a protected amino group;
reacting the compound of formula XI with a leaving group forming agent of the formula LG*-X wherein LG* is an electrophilic radical capable of forming, with a hydroxy to which it is bound, a leaving group LG2, and X is halogen, to yield a compound of formula XII:

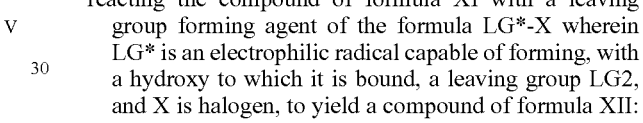

wherein R₁ is a secondary amino protecting group, R₂ is a protected amino group, and LG2 is a leaving group; and
cyclizing the compound of formula XII under basic conditions to yield the compound of formula XIII.

14. The method of claim 13, wherein the compound of formula X is obtained by reacting a compound of formula VIII:

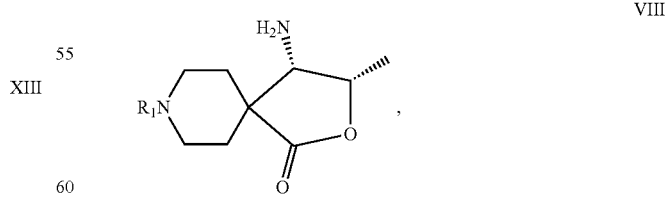

wherein R₁ is a secondary amino protecting group, with an amino protecting group to yield the compound of formula X.

15. The method of claim 14, wherein the compound of formula VIII is obtained by hydrogenating a compound of formula VII:

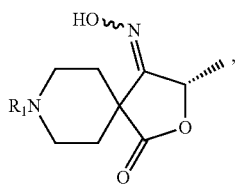

wherein R₁ a secondary amino protecting group, to yield the compound of formula VIII.

16. The method of claim 15, wherein the compound of formula VII is obtained by cyclizing a compound of formula VI:

VI

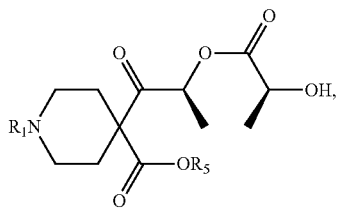

wherein R₁ a secondary amino protecting group and R₅ is unsubstituted or substituted alkyl, unsubstituted or substituted cycloalkyl or unsubstituted or substituted aryl, with hydroxylamine, or a salt thereof, to yield the compound of formula VII;

or alternatively by reacting a compound of formula VI*:

VI*

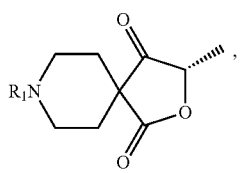

wherein R₁ is a secondary amino protecting group, with hydroxylamine, or a salt thereof, to yield the compound of formula VII.

17. The method of claim 16, wherein the compound of formula VI or the compound of formula VI* is obtained by reacting a compound of formula V:

V

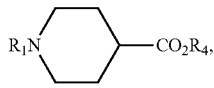

wherein R₁ is a secondary amino protecting group and R₄ is a carboxyl (—COOH) protecting group, in the presence of a strong base with L-lactide of the formula:

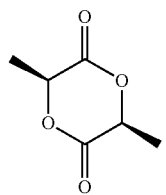

to yield the compound of formula VI or alternatively the compound of formula VI*.

18. The method of claim 15, wherein the compound of formula VII is obtained by reacting a compound of formula V:

V

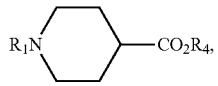

wherein R₁ is a secondary amino protecting group and R₄ is a carboxyl (—COOH) protecting group, in the presence of a strong base with L-lactide of the formula:

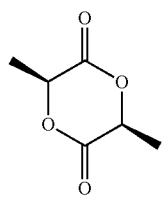

to provide an intermediate; and
  subsequently reacting the intermediate with hydroxylamine, or a salt thereof, to yield the compound of formula VII.

19. The method of claim 1, wherein A is a halogenide anion.

20. The method of claim 1, wherein the compound of formula II has the following structure:

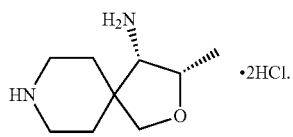

21. The method of claim 1, wherein LG is halo.

22. The method of claim 1, wherein the compound of formula III has the following structure:

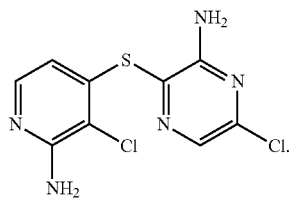 [SMILES: Nc1nc(Cl)cnc1Sc1ccnc(N)c1Cl]

23. A method for the manufacture of a compound of Formula I:

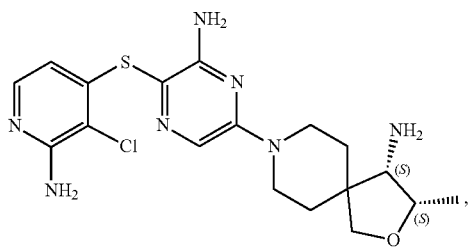

or a pharmaceutically acceptable salt, acid co-crystal, hydrate or other solvate thereof, said method comprising:
reacting a compound of formula V:

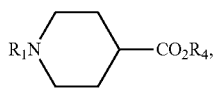

wherein $R_1$ is tert-butoxycarbonyl, and $R_4$ is a carboxyl (—COOH) protecting group, in the presence of a strong base with L-lactide of the formula:

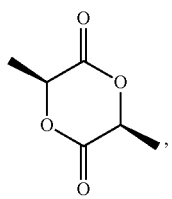

to provide an intermediate, and subsequently reacting the intermediate with hydroxylamine, or a salt thereof, to yield a compound of formula VII:

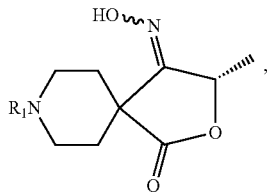

wherein $R_1$ tert-butoxycarbonyl;
hydrogenating the compound of formula VII to yield a compound of formula VIII:

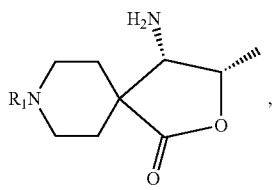

wherein $R_1$ is tert-butoxycarbonyl;
reacting the compound of formula VIII with an amino protecting group to yield a compound of formula X:

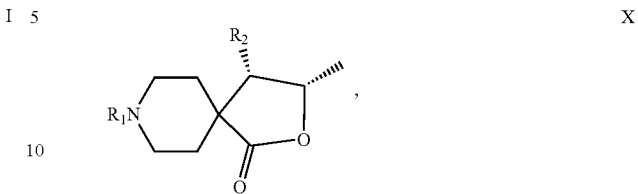

wherein $R_1$ is tert-butoxycarbonyl, and $R_2$ is a protected amino group;
reducing the compound of formula X to yield a compound of formula XI:

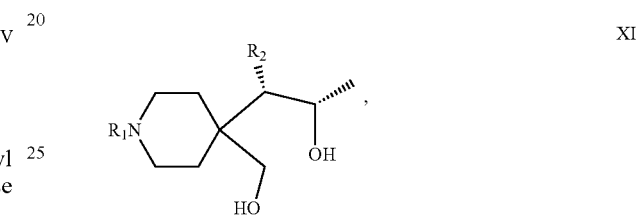

wherein $R_1$ is tert-butoxycarbonyl, and $R_2$ is a protected amino group;
reacting the compound of formula XI with a leaving group forming agent of the formula LG*-X wherein LG* is an electrophilic radical capable of forming, with a hydroxy to which it is bound, a leaving group LG2, and X is halogen, to yield a compound of formula XII:

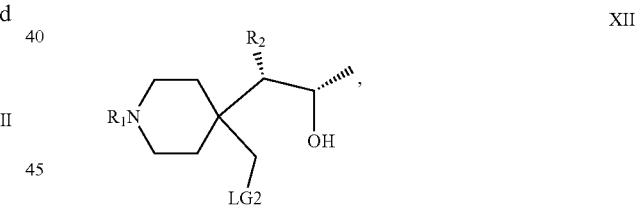

wherein $R_1$ is tert-butoxycarbonyl, $R_2$ is a protected amino group, and LG2 is a leaving group;
cyclizing the compound of formula XII under basic conditions to yield a compound of formula XIII:

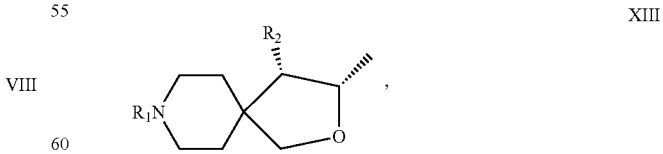

wherein $R_1$ is tert-butoxycarbonyl, and $R_2$ is a protected amino group;
deprotecting the compound of formula XIII, and if required, reacting the resulting compound with HCl to yield a compound of formula II:

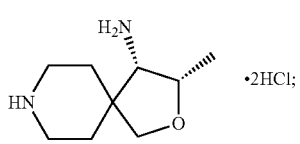
and
reacting the compound of formula II with a compound of formula III:
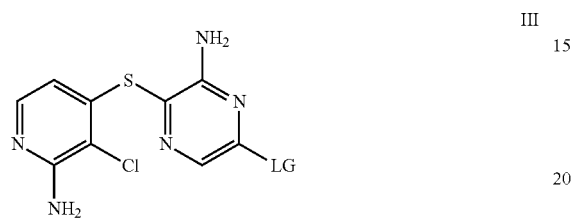
to yield the compound of Formula I.
* * * * *